(12) United States Patent
Du et al.

(10) Patent No.: US 9,670,462 B2
(45) Date of Patent: Jun. 6, 2017

(54) BIOACTIVE SURFACE FOR HEPATOCYTE-BASED APPLICATIONS

(75) Inventors: Yanan Du, Nanos (SG); Rongbin Han, Nanos (SG); Hanry Yu, Nanos (SG)

(73) Assignee: Agency for Science, Technology and Research, Singapore (SG)

( * ) Notice: Subject to any disclaimer, the term of this patent is extended or adjusted under 35 U.S.C. 154(b) by 1683 days.

(21) Appl. No.: 12/301,890

(22) PCT Filed: May 24, 2007

(86) PCT No.: PCT/SG2007/000147
§ 371 (c)(1),
(2), (4) Date: Aug. 18, 2010

(87) PCT Pub. No.: WO2007/136354
PCT Pub. Date: Nov. 29, 2007

(65) Prior Publication Data
US 2011/0053783 A1    Mar. 3, 2011

Related U.S. Application Data

(60) Provisional application No. 60/802,768, filed on May 24, 2006.

(51) Int. Cl.
| | |
|---|---|
| C40B 30/00 | (2006.01) |
| C12Q 1/00 | (2006.01) |
| C12N 11/08 | (2006.01) |
| C12N 5/071 | (2010.01) |
| C12N 5/00 | (2006.01) |
| C12M 1/00 | (2006.01) |

(52) U.S. Cl.
CPC ......... *C12N 5/0677* (2013.01); *C12N 5/0068* (2013.01); *C12N 5/0671* (2013.01); *C12N 2533/20* (2013.01); *C12N 2533/30* (2013.01); *C12N 2533/50* (2013.01); *C12N 2533/52* (2013.01); *C12N 2533/54* (2013.01)

(58) Field of Classification Search
CPC ........... C40B 30/00; C12M 1/00; C12N 11/08
USPC .......................................................... 506/7
See application file for complete search history.

(56) References Cited

U.S. PATENT DOCUMENTS

| | | | |
|---|---|---|---|
| 6,197,575 B1* | 3/2001 | Griffith et al. | 435/288.4 |
| 8,143,042 B2* | 3/2012 | Bettinger et al. | 435/180 |
| 2005/0058685 A1* | 3/2005 | Mao et al. | 424/426 |

FOREIGN PATENT DOCUMENTS

| | | |
|---|---|---|
| EP | 587205 A1 * | 3/1994 |
| WO | WO 99/52560 A1 | 10/1999 |
| WO | WO 2004/027050 A1 | 4/2004 |

OTHER PUBLICATIONS

Park et al (Biotechnology Letters 24: 1401-1406, 2002).*
Kobayashi et al(Nippon Kagaku Kaishi, vol. 1987(187), No. 3, pp. 575-579),(abstract only).*
Wu, Y., Study of Galactosylated Collagen as ECM in 3-D Hepatocyte Culture in Vitro, Thesis, National University of Singapore, 2005, 1-172.*
Score Search Results; 20140902_131935_us-12-301-890-3.rag, 2014, 1-25.*
Gestwicki et al., Selective Immobilization of Multivalent Ligands for Surface Plasmon Resonance and Fluorescence Microscopy, Analytical Biochemistry, 2002, 305, 149-155.*
Du et al., Identification and Characterization of a Novel Prespheroid 3-Dimensional Hepatocyte Monolayer on Galactosylated Substratum, Tissue Engineering, 2007, 13(7), 1455-1468.*
Du et al., Synthetic Sandwich Culture of 3D Hepatocyte Monolayer, Biomaterials, 2008, 29, 290-301.*
Oka et al., Binding and Spreading of Hepatocytes on Synthetic Galactose Culture Surfaces Occur as Distinct and Seperable Threshold Responses, The Journal of Cell Biology, 1986, 103, 1055-1060.*
Mrksich, M., Using Self-Assembled Monolayers to Model the Extracellular Matrix, Acta Biomaterialia, 2009, 5, 832-841.*
Otsuka, H., Nanofabrication of Nonfouling Surfaces for Micropatterning of Cell and Microtissue, Molecules, 2010, 15, 5525-5546.*
Mendes, P., Stimuli-Responsive Surfaces for Bio-Applications, Chem. Soc. Rev., 2008, 37, 2512-2529.*
Begovac et al., "Cell surface galactosyltransferase mediates the initiation of neurite growth from PC12 cells on laminin," Feb. 1990, The Journal of Cell Biology, vol. 110, pp. 461-470.
Cho et al., "Galactose-carrying polymers as extracellular matrices for liver tissue engineering," Biomaterials, 2006, vol. 27, pp. 576-585.
De Bartolo, L. et al., "Biotransformation and liver-specific functions of human hepatocytes in culture on RGD-immobilized plasma-processed membranes," *Biomaterials*, 2005, vol. 26, pp. 4432-4441.
Du, Y. et al., "3D hepatocyte monolayer on hybrid RGD/galactose substratum," *Biomaterials*, 2006, vol. 27, pp. 5669-5680.
Du, Y. et al., "Identification and Characterization of a Novel Prespheroid 3-Dimensional Hepatocyte Monolayer on Galactosylated Substratum," *Tissue Engineering*, 2007, vol. 13, No. 7, pp. 1455-1467.
Gutsche, A.T. et al., "Synthesis and Characterization of Polymer Substrates for Rat Hepatocyte Culture," *Material Research Society Symposium Proceedings*, 1994, vol. 330, pp. 243-248.
International Search Report mailed on Aug. 30, 2007, for International Application No. PCT/SG2007/000147, filed on May 24, 2007, 3 pages.
Lopez, L.C. et al., "Galactose immobilization on plasma processed polymers for biomedical applications," *Journal of Applied Biomaterials and Biomechanics*, 2004, vol. 2, p. 211.

(Continued)

*Primary Examiner* — Amy M Bunker
(74) *Attorney, Agent, or Firm* — Kilpatrick Townsend & Stockton LLP

(57) ABSTRACT

The invention provides a surface, wherein said surface comprises (i) a polymer substrate and (ii) sugar groups and peptide groups coupled to said substrate suitable for culturing hepatocytes.

6 Claims, 20 Drawing Sheets

(56) References Cited

OTHER PUBLICATIONS

Na, K. et al., "Conjugation of Arg-Gly-Asp (RGD) Sequence in Copolymer Bearing Sugar Moiety for Insulinoma Cell Lin (MIN6) Culture," *Bioscience Biotechnology and Biochemistry*, 2001, vol. 65, No. 6, pp. 1284-1289.

Park, K-H. et al., "Immobilization of Arg-Gly-Asp (RGD) Sequence in Sugar Containing Copolymer for Culturing of Pheochromocytoma (PC12) Cells," *Journal of Bioscience and Bioengineering*, 2004, vol. 97, No. 3, pp. 207-211.

Park, K-H. et al., "Phenotype of Hepatocyte Spheroids in Arg-Gly-Asp (RGD) Containing a Thermo-Reversible Extracellular Matrix," *Bioscience Biotechnology and Biochemistry*, 2002, vol. 66, No. 7, pp. 1473-1478.

Yin, C. et al., "High density of immobilized galactose ligand enhances hepatocyte attachment and function," *Journal of Biomedical Materials Research*, 2003, vol. 67, pp. 1093-1104.

Ying, L. et al., "Immobilization of Galactose Ligands on Acrylic Acid Graft-Copolymerized Poly(ethylene terephthalate) Film and Its Application to Hepatocyte Culture," *Biomacromolecules*, 2003, vol. 4, pp. 157-165.

Chua, K.N. et al., "Stable Immobilization of Rat Hepatocyte Spheroids on Galactosylated Nanofiber Scaffold," Biomaterials 26:2537-2547 (2005).

Ijima, H. et al., "Promotion of Monolayer Formation and High Expression of Ammonia Metabolism of Primary Rat Hepatocytes on Arginine-Glycine-Aspartic Acid-Containing Peptide-Coated Polystyrene Dish," J. Biosci. Bioeng. 100(1):62-66 (2005).

Ng, S. et al., "Optimization of 3-D Hepatocyte Culture by Controlling the Physical and Chemical Properties of the Extra-Cellular Matrices," Biomaterials 26:3153-3163 (2005).

\* cited by examiner

```
                        SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: synthetic cell adhesion peptide

<400> SEQUENCE: 1

Tyr Ile Gly Ser Arg
1               5

<210> SEQ ID NO 2
<211> LENGTH: 6
<212> TYPE: PRT
<213> ORGANISM: Artificial Sequence
<220> FEATURE:
<223> OTHER INFORMATION: synthetic cell adhesion peptide
<220> FEATURE:
<221> NAME/KEY: MOD_RES
<222> LOCATION: (3)...(3)
<223> OTHER INFORMATION: Xaa = hydroxyproline (Hyp)

<400> SEQUENCE: 2

Gly Phe Xaa Gly Glu Arg
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic cell adhesion peptide, soluble RGD
      peptide

<400> SEQUENCE: 3

Gly Arg Gly Asp Ser
1               5
```

BIOACTIVE SURFACE FOR HEPATOCYTE-BASED APPLICATIONS

RELATED APPLICATIONS

This application claims the benefit of U.S. Provisional Application No. 60/802,768 filed 24 May 2006, the disclosures of which are incorporated herein by reference in their entirety.

TECHNICAL FIELD

The present invention relates to the stabilisation of a hepatocyte monolayer culture through a bioactive substratum. The present invention further relates to the use of the hepatocyte monolayer cultures for hepatocyte-based applications.

BACKGROUND OF THE INVENTION

Cells dissociated from a variety of tissues such as the mammary gland, the pancreatic islet, the lung or liver have been demonstrated to be capable under appropriate experimental conditions to self-assemble into multicellular aggregates with organization and architecture which resembles their original tissue. The ability to understand and control the morphogenesis of these three dimensional tissue-like structures is a fundamental objective of cell and developmental biology and tissue engineering research.

In the field of liver tissue engineering, self-assembled spheroidal aggregates of isolated primary hepatocytes have been obtained in suspension culture or by utilizing moderately-adhesive substrata of natural or artificial extracellular matrices such as laminin, fibronectin or collagen I. The extracellular matrix proteins mentioned above may be conjugated with cell adhesion peptides, such as Arg-Gly-Asp (RGD) and Tyr-Ile-Gly-Ser-Arg (YIGSR; SEQ ID NO:1)). However, hepatocytes adhere tightly to these substrata, which results in extended and spread cell morphology, and low levels of liver-specific activities which may be a result of hepatocyte de-differentiation.

In contrast, if hepatocytes are anchored too loosely to the substrata, hepatocyteaggregate into spheroids which form in vivo-like 3D architecture and which exhibit tissue-like cell-cell and cell-matrix connectivity and enhanced liver-specific activities, membrane polarities and liver ultrastructure, such as bile canaliculi, tight junctions and gap junctions. The features of hepatocyte spheroids suggest their potential applications in bioartificial liver aided devices (BLAD) and drug metabolic/hepatotoxicity studies.

However, the usefulness of 3D hepatocyte spheroids is limited due to the poor mass transport of nutrients, oxygen, xenobiotics and metabolites into and from the core of these large cellular aggregates. Cell loss is also a critical issue in forming and maintaining these spheroids due to the poor adhesion of spheroids on the substratum. Accordingly, an alternative to producing hepatocyte spheroids which offers some of the advantageous properties of spheroids but avoids some of the disadvantages of spheroids is desirable.

SUMMARY OF THE INVENTION

According to a first aspect, there is provided a surface, wherein said surface comprises (i) a polymer substrate and (ii) sugar groups and peptide groups coupled to said substrate.

According to another aspect, there is provided a device having a surface according to the first aspect.

According to another aspect, there is provided a process for providing a stabilized culture of hepatocytes, comprising:

providing a surface which comprises a polymer substrate, sugar groups and peptide groups coupled to the polymer substrate;

incubating the surface in the presence of hepatocytes in vitro for a time and under conditions suitable for the adhesion of the hepatocytes to the surface, and culturing the hepatocytes which are adherent to the surface to produce a stabilized culture of hepatocytes.

According to another aspect, there is provided a process for making a polymeric surface comprising the step of coupling a sugar group and a peptide group to a polymer substrate.

The process may further comprise the step of grafting a second polymer onto a first polymer to form the polymer substrate prior to the step of coupling. The grafting of the second polymer onto the first polymer may comprise plasma treatment and/or UV-induced grafting polymerization. The plasma treatment may be argon-plasma treatment.

The step of coupling may comprise:
a) activating the polymer substrate to form an activated polymer substrate; and
b) reacting the activated polymer substrate with a first reagent comprising the sugar group and a second reagent comprising the peptide group to form the surface.

The step of activating may comprise reacting the polymer substrate with an activating reagent to attach activating groups to the surface of the polymer substrate.

The step of coupling may further comprise a step of quenching the polymeric substrate with a quenching reagent, thereby quenching unreacted activating groups.

The activating reagent may comprise N-hydroxysuccinimido (NHS) groups and both the first reagent and the second reagent may each comprise at least one amine group.

The quenching reagent may comprise amine groups.

According to a further aspect, there is provided a bioreactor for culturing hepatocytes, wherein said bioreactor comprises a surface which comprises (i) a polymer substrate and (ii) sugar groups and peptide groups coupled to said substrate. The bioreactor may be in the form of a membrane, a tube, a microtiter well, a column, a hollow fiber, a roller bottle, a tissue culture plate, or a microcarrier.

According to another aspect, there is provided a use of a surface which comprises (i) at least one polymer substrate and (ii) sugar groups and peptide groups coupled to said substrate, in a bioartificial liver aided device (BLAD). The BLAD may be a bioreactor.

According to another aspect of the present invention there is provided a device for growing hepatocytes, wherein said device comprises a surface comprising (i) at least one polymer substrate and (ii) sugar groups and peptide groups coupled to said substrate. The device may be a BLAD. The BLAD may be a bioreactor.

According to any of the above aspects, the polymer substrate may comprise a thermoplastic polymer, such as a polyester. The polymer substrate may comprise a polymer which is graftable by means of plasma or UV methods. In one embodiment, the polyester is polyethylene terephthalate. The polymer substrate may comprise a first polymer and a second polymer grafted to the first polymer. The sugar groups and peptide groups may be coupled to the second polymer. The second polymer may be polyacrylic acid.

The sugar groups may comprise at least one monosaccharide group. In one embodiment the monosaccharide is a hexose, such as galactose. In yet another embodiment, the galactose may be a lactose.

In one embodiment of any of the above aspects, the peptide groups comprise peptides which are three to ten amino acid residues in length. These peptide groups may be derived naturally or synthetically. The peptide group may be RGD peptide and/or a YIGSR peptide (SEQ ID NO:1) and/or a GFOGER peptide (SEQ ID NO:2). The peptide group may be RGD peptide, such as GRGDS (SEQ ID NO:3). In one embodiment, the peptide group is GRGDS. In another embodiment, the peptide group is YIGSR (SEQ ID NO:1). In yet another embodiment, the peptide group is GFOGER (SEQ ID NO:2).

In certain embodiments of any of the above aspects, the surface may be porous to the passage of water, salts, or glucose. In other embodiments the surface may be impermeable.

BRIEF DESCRIPTION OF THE FIGURES

A preferred embodiment of the present invention will now be described, by way of examples only, with reference to the accompanying figures wherein.

DEFINITIONS

Figure 1:
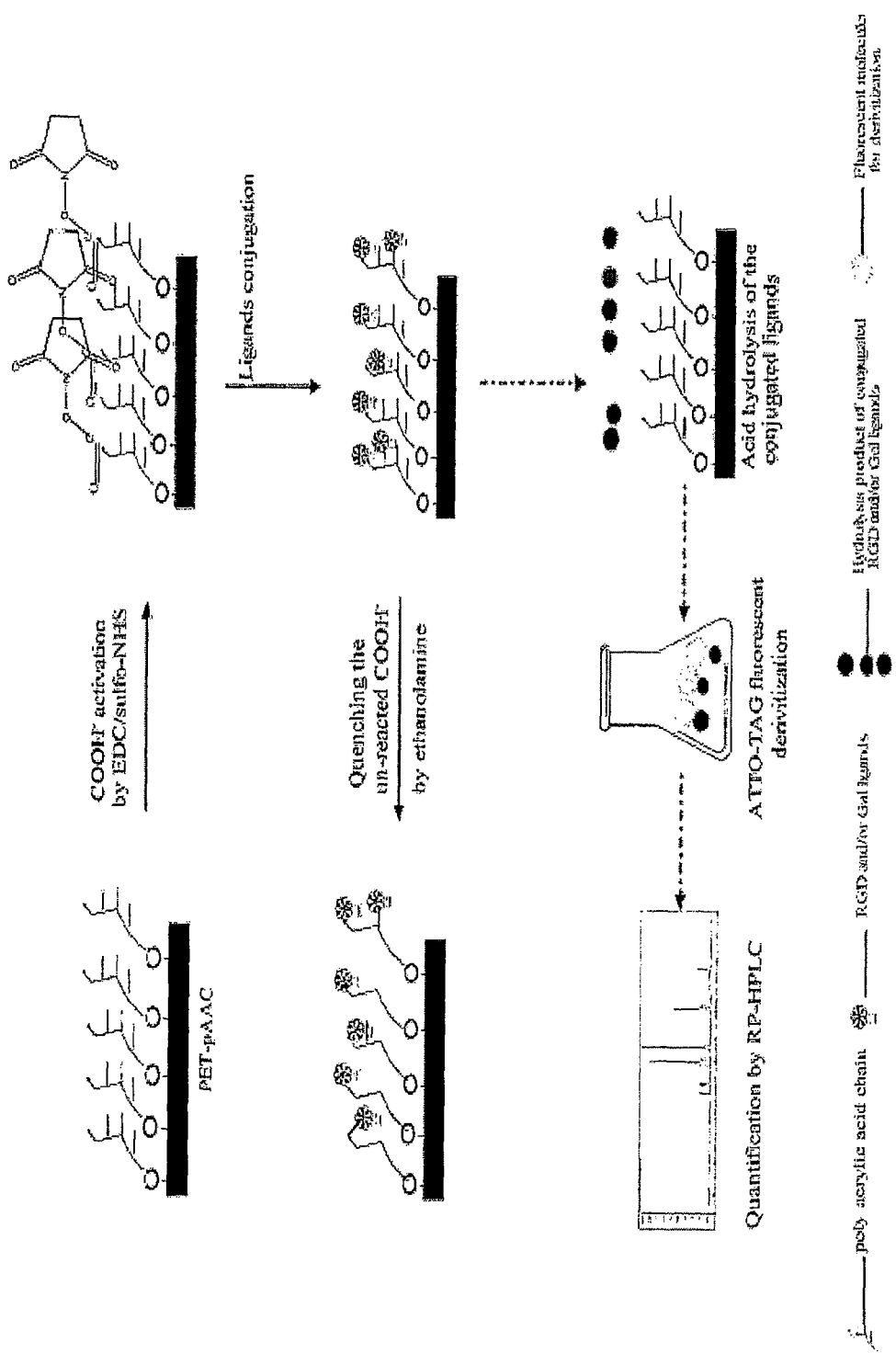
FIG. 1. Schematic diagram of ligands conjugation onto the PET-pAA (polyacrylic acid) film by a 2-step reaction scheme (solid arrow) and quantitative analysis of the conjugated ligands by reverse-phase high performance liquid chromatography (RP-HPLC; dotted arrow).

Throughout this specification, unless the context requires otherwise, the word "comprise", or variations such as "comprises" or "compromising", will be understood to imply the inclusion of a stated step or element or integer or group of steps or elements or integers but not the exclusion of any one step or element or integer or group of elements or integers.

As used herein the term "derived from" shall be taken to indicate that a specified integer may be obtained from a particular source albeit not necessarily directly from that source.

As used herein the term "ROD peptide" shall be taken to mean a peptide that comprises the amino acid residues Arg-Gly-Asp. Peptides containing RGD may specifically bind to integrins expressed on the surface of cells via RGD recognition sites (Plow et al., J Biol Chem, 2000). An RGD peptide may contain one or more amino acids flanking the RGD motif.

As used herein the term "3D spheroids" shall be taken to mean the formation of cultured hepatocytes in a 3D architecture, usually in the form of rounded aggregates wherein at least one of the following features is present: (i) well established cell-cell/cell-matrix interactions such as the polarized expression of E-cadherin, (ii) possessing activities specific to the liver, (iii) exhibiting membrane polarity and (iv) possessing ultrastructures which are presented by hepatocytes in vivo in a greater extent than hepatocytes cultured on a collagen substrate.

It will be understood that the term "3D hepatocyte monolayer" is used herein to mean the monolayer of hepatocytes in culture which results when hepatocytes are cultured on a surface which comprises sugar groups such as galactose and peptide groups such as RGD peptides. The hepatocytes in a 3D hepatocyte monolayer exhibit cell spreading, but also exhibit many of the characteristics of hepatocytes present in the 3D spheroids as described above.

As used herein, the term "stabilizing" or "stable" or "stabilized" shall be taken to mean the prolonged existence of the 3D hepatocyte monolayer as described above such that the transient cell-spreading phase which occurs between 2 cycles of cell-aggregation phases becomes a less transient cell-spreading phase. A stabilized culture of hepatocytes is a monolayer comprising the cell-spreading phase which takes place for at least approximately 24 hours.

As used herein, the term "integrin" represents a plasma membrane receptor which mediates cell adhesion by binding to a RGD ligand.

As used herein, the term "galactose" or "galactose ligand" is an example of a sugar group. Sugar groups and peptide groups can be coupled onto a polymer substrate.

DETAILED DESCRIPTION OF THE PREFERRED EMBODIMENTS

As described herein, the invention provides a surface comprising (i) at least one polymer substrate, such as a polyethylene terephthalate film, and (ii) sugar groups such as galactose and peptide groups such as RGD peptides which are conjugated (coupled) to the polymer substrate. The RGD peptides and galactose on the polymer substrate enhance cell adhesion to the substrate and liver-specific activities as described herein.

Pretreatment of Polymer Substrate

The polymer substrate may be activated prior to coupling the sugar groups and peptide groups thereto. This activation may occur by implementing a pre-treatment step which allows the substrate to react with the sugar groups such as galactose and peptide groups such as RGD peptides and form the surface. The substrate may be activated by a chemical reaction, that being the addition of an activating reagent. A suitable activating reagent may have a functional group capable of coupling to the polymer substrate and a separate functional group capable of reacting with the first and second reagents, which contain the sugar group and the peptide group respectively. Alternatively it may be capable of activating the reaction of the first and second reagents with the polymer substrate. In one embodiment, the first and second reagents at least comprise one amine group and the polymer substrate has surface carboxyl groups. In this embodiment, a suitable activating reagent is N-hydroxysuccinimide. This reagent is capable of reacting with surface carboxyl groups on the polymer, and may subsequently be displaced by amine groups on the first and second reagents in order to couple the first and second reagents to the polymer substrate via amide groups. Another suitable reagent is dicyclohexylcarbodiimide (DCC). Other similar activating reagents will be readily apparent to those skilled in the art.

Polymer Substrate

Polymer substrates as provided in the invention may belong to the group of polymers known as thermoplastic polymers. In one embodiment, a thermoplastic polymer may be a polyester. In another embodiment the polyester may be polyethylene terephthalate. The polymer substrate may comprise a first polymer having a second polymer grafted thereto. The second polymer may be an addition polymer. It may be a poly acid such as a polyacrylic acid or polymethacrylic acid. In one embodiment, the first polymer, such as PET, may be functionalized by grafting polyacrylic acid or polymethylacrylic acid (optionally substituted on the methyl group) to introduce the carboxylic acid groups. The second polymer may be attached to a first polymer by graft polymerization. However, other suitable techniques for fixing may be used as contemplated by a person skilled in the art. Grafting may be performed using for example, plasma treatment such as argon-plasma treatment, and/or UV-induced copolymerization.

Sugar Groups

It is contemplated herein that the sugar groups may be monosaccharides. A monosaccharide may be a hexose or a derivative thereof. The hexose may be galactose. The sugar group may be any sugar comprising galactose moieties, such as lactose Peptide Groups The present invention provides peptide groups. These peptide groups may be capable of binding to an integrin. An example of these peptide groups us a tripeptide or a YIGSR peptide. The tripeptide may be an RGD peptide. (Tyr-Ile-Gly-Ser-Arg (YIGSRI SEQ ID NO:1)) [Carlisle et al., Tissue Eng 2000], Gly-Phe-Hyp-Gly-Glu-Arg (GFOGER; SEQ ID NO:2)) [Reyes et al. J Biomed Mater Res A 2003].

Surface

The present invention provides a surface which may be porous or impermeable. The surface may be a monolayer or multilayered. The surface may be in the form of a membrane, tube, microtiter wells, columns, hollow fibers, roller bottles, plates, and microcarries.

Conjugation

As described herein, conjugation can be any chemistry that is used to conjugate sugar groups such as galactose and peptide groups such as RGD peptides wherein these groups may be conjugated to each other and/or to a substratum in order to produce a surface which is suitable to perform the invention. As described herein, coupling can be conjugation.

Without being limited to the particular examples described herein, it will be understood that the following examples describe chemistries which may be used to couple the sugar groups and the peptide groups to a substrate.

a carboxylic acid group on a substratum may be coupled with galactose ligands and RGD peptides (or derivative thereof) containing an amine group to form an amide group;

an N-hydroxysuccinimido ester of a carboxylic acid on a substratum may be coupled with galactose ligands and RGD peptides (or derivative thereof) containing an amine group to form an amide group;

an amine group on a substratum may be coupled with galactose ligands and RGD peptides (or derivative thereof) having an acid chloride to form an amide group;

an azide group on a substratum may be coupled with galactose ligands and RGD peptides (or derivative thereof) having an acetylenic group to form a triazole group;

a maleimido group on a substratum may be coupled with galactose ligands and RGD peptides (or derivative thereof) having a thiol group via a Michael type addition to produce an N-hydroxysuccinimido thioether group.

It will be understood, however, that numerous other functional groups and activation strategies commonly employed in the art to specifically immobilise biological molecules to polymer surfaces may also be employed. Other coupling reactions that are well known in the art may also be used. These may comprise any of the well known methods of introducing chemical groups into a molecule or onto a functionalised solid. These include nucleophilic substitution of a benzyl halide (e.g. chloride or bromide) group, "click" chemistry etc. Suitable click chemistry may include for example cycloaddition reactions, such as the Huisgen 1,3-dipolar cycloaddition, Cu(I) catalyzed azide-acetylene cycloaddition, Diels-Alder reaction, nucleophilic substitution to small strained rings (e.g. epoxy and aziridine rings), formation of ureas and amides and addition reactions to double bonds, e.g. epoxidation, dihydroxylation.

This invention is based on the surprising finding that hepatocytes which are cultured on galactose-conjugated bioactive substrata undergo 2 cycles of cell-aggregation and spreading to form large spheroids. Between the first and second cell-aggregation phases, there is a cell-spreading phase in which the hepatocytes attach to the substrata as monolayer but exhibit many characteristics of the 3D spheroids, such as well-established cell-cell/cell-matrix interactions, high levels of metabolic, synthetic, detoxification and excretory functions but without the above-described limitations of the 3D spheroids such as poor mass transfer and un-even spatial distributions of cells with different characteristics. The cell-spreading phase (termed "3D hepatocyte monolayer") occurs only transiently between the two cell-aggregation phases, occurring between one and three days and lasting only about 24 hrs In employing a surface comprising a polymer surface and sugar groups such as galactose and peptide groups such as RGD peptides, it was found to stabilize the 3D hepatocyte monolayer in the cell-spreading phase over a period of up to approximately a week, so as to enable useful applications of this 3D hepatocyte monolayer.

In order to achieve stabilization of this 3D hepatocyte monolayer for hepatocyte based applications, the present inventors modified a bioactive galactosylated substratum which comprises conjugated galactose on polyethylene terephthalate (PET) film (U.S. Publication No. 2005-0058685 A1 incorporated herein by reference) by co-conjugating RGD peptide and galactose onto the PET film.

Without being bound by any proposed mechanisms, it is thought that the stronger cell-substratum interaction mediated by the RGD peptide and integrins at the surface of cultured hepatocytes selectively stabilize the cell-spreading 3D monolayer phase. The 3D monolayer structure is stable on this hybrid substratum up to one week, which would be useful for various hepatocyte-based/liver engineering applications requiring both effective mass transfer and cellular support such as in drug metabolism, hepatotoxicity studies or BLAD. In the exemplary hepatotoxicity study, the 3D hepatocyte monolayer cultured on the PET-hybrid substratum exhibited a high level of sensitivity to hepatotoxicity which is induced by the model drug acetaminophen. This sensitivity is similar to the 3D spheroids but higher than 2D hepatocyte monolayers cultured on a collagen-coated substratum.

By studying the dynamics of E-Cadherin, phosphorylated focal adhesion kinase (p-FAK) and F-actin distribution and expression during spheroid formation, it was found that hepatocyte morphogenesis on the galactosylated substratum was mainly regulated by the balance between cell-cell interaction and cell-substratum interaction through cytoskeletal reorganization. During different stages of hepatocyte spheroid formation, hepatocytes in a pre-spheroid monolayer stage possessed strong cell-substratum interactions and cell-cell interactions when compared with a conventional hepatocyte 2D monolayer cultured on collagen-coated substratum. Hepatocytes in this transient pre-spheroid monolayer stage exhibited improved cellular structure and polarities, enhanced cell-cell interaction and better differentiated activities, which are comparable with hepatocytes in 3D spheroids without the mass transport problem mentioned in the background section.

In order to stabilize the pre-spheroid monolayer structure for a longer period of application (e.g. from approximately 1 day to 5-10 days, for example about 7 days), a RGD peptide was co-conjugated onto the galactosylated substratum to enhance cell-substratum interactions mediated by RGD-integrin binding. Primary hepatocytes have been widely used in bioartificial liver aided devices (BLAD) and in pharmacological, toxicological and metabolic studies. Hepatocytes in these applications are typically grown on appropriate substrata to achieve optimal cell attachment and functional maintenance [Allen et al., Hepatology, 2001; Sep; 34(3):447-455; LeCluyse et al., Pharma Biotechnol, 1996; 8:121-159; Lu et al., Biomaterials, 2003Dec.; 4(27) 4893-4903]. A variety of natural or synthetic polymeric substrata have been employed for hepatocyte cultures (e.g. plastic surfaces or membranes coated with extracellular matrix proteins such as collagen, laminin, fibronectin or conjugated with cell adhesion peptides, such as Arg-Gly-Asp (RGD) [Tashiro et al., J Cell Physiol, 1991, Mar.; 146(3) 451-459] and Tyr-Ile-Gly-Ser-Arg (YIGSR; SEQ ID NO:1) [Carlisle et al, Tissue Eng. 2000, Feb.; 6(1):45-52]). Hepatocytes anchor tightly to these substrata, and exhibit extended and spread cell morphology, with low levels of liver-specific functions likely due to hepatocyte de-differentiation [Ying et al, Biomacromolecules 2003, Jan.-Feb.; 4(1):157-165]. These substrata have been extensively used for drug screening in microplates [Gebhardt et al., Drug Metab Rev 2003, May-Aug.; 35(2-3):145-213; Coecke et al., ATLA 1999; 27:579-638; Kikkawa et al., J Toxicol Sci 2005, Feb.; 30(1):61-72] as well as for BLAD bioreactors [Park et al., J Biosci Bioeng 2005, Apr.; 99(4)311-319]. Galactose-conjugated substrata are attractive alternatives for hepatocyte attachment through the galactose-asialoglycoprotein receptor (ASGPR) interaction.

An embodiment of the invention relates to a bioactive substratum by conjugating both RGD peptide groups and galactose to a polymer such that hepatocytes can anchor stably onto the substratum as a monolayer while maintaining the non-spread cell morphology, tight cell-cell interactions and high levels of liver-specific activities typically seen in 3D hepatocyte spheroids.

In one embodiment, PET film was surface-modified with polyacrylic acid (pAA) (see Example 1A) followed by conjugation using a 'two-step' 'EDC' chemistry (see Example 1B) and characterized with X-ray photoelectron spectroscopy (XPS) and reverse phase high performance liquid chromatography (RP-HPLC). The PET film conjugated with both the RGD peptide and galactose (PET-hybrid) was inserted into 96-well microplates for hepatocyte culture, with PET film conjugated with only RGD peptide (PET-RGD), galactosylated PET (PET-Gal) and collagen-coated microplates as controls. Analyses of the expression of key markers (F-actin, E-cadherin, P-FAK) indicated that the cells on PET-hybrid membrane behave like cells in 3D spheroids even though they adhere to the 2D substratum. The 3D hepatocyte monolayer cultured on PET-hybrid also exhibited similar sensitivity to acetaminophen-induced hepatocytotoxicity as the 3D hepatocyte spheroids rather than the 2D controls. This hybrid RGD/galactose bioactive substratum supports spheroid-like hepatocyte behaviors on monolayer, avoiding the cell loss and mass transfer limitation of typical 3D spheroids, and can be immediately adopted in microplates or other prevailing 2D culture devices or bioreactors for various applications.

An aspect of this invention is the development of a hybrid bioactive substratum for hepatocytes culture which contains both a peptide group for attachment enhancement such as a RGD peptide and a sugar group such as galactose, for morphological and hepatic functional improvement. When primary hepatocytes are cultured on the hybrid substratum with both RGD and galactose, a synergistic interplay between these two ligand-receptor interactions was observed.

An intermediate morphological state between the spreading monolayer and the 3D monolayer was observed in which hepatocytes contact each other with tight cell-cell interactions and at the same time with effective adhesion to the substratum. Differentiated activities, detoxification capacity and responsive sensitivity to hepatotoxicity of the hepatocyte '3D monolayer' were similar to 3D spheroids. Interestingly, based on the live imaging study of the dynamic spheroid formation on PET-Gal, there also exits a 'monolayer' stage between the pre-spheroid stage which is within one day post cell seeding and a compact 3D spheroid stage which occurs after three days post cell seeding. 3D spheroids form when small pre-spheroids gradually spread and merge with each other thus temporarily forming a monolayer which subsequently results in larger and more compact mature spheroids.

Also contemplated herein are cell culture surfaces for bioreactors in the field of liver tissue engineering. It may provide methods of improving the surfaces to obtain 3D hepatocyte monolayer, a culture configuration with better cell attachment and function.

Model System to Study the Mechanism of Tissue Morphogenesis

The ability to understand and control the morphogenesis of 3D tissue-like structures is a fundamental objective of cell and developmental biology and tissue engineering research. Hepatocyte spheroid formation involves cell translocation and changes in cell shape that mimic the process of tissue formation. The capacity to regulate hepatocytes spheroid formation by the bioactive ligands in the hybrid polymeric substratum enables the mechanism study of spheroid formation.

"Supporting Surface" for Bio-Artificial Liver Bioreactor

Bioreactors for bio-artificial liver devices may be in any suitable form, such as membrane, tubes, microtiter wells, columns, hollow fibers, roller bottlers, plates, and microcarriers. The "supporting surface" of a bioreactor is intended to physically contact and support the attachment of the cells. Suitable support materials provide a surface that exhibits an optimal combination of such properties as rigidity, surface area, ease of preparation and use, and cost.

The present invention provides commercial impetus to elucidate the mechanisms of spheroids self-assembly on galactosylated bioactive substrata which potentially direct the design of more appropriate bioactive biomaterials. In addition, the identification and stabilization of the pre-spheroid monolayer provides a useful configuration for liver tissue engineering applications such as BLAD and drug metabolism/hepatotoxicity studies.

Identification of a pre-spheroid 3D hepatocyte monolayer and the stabilization of this configuration by using the RGD/galactose hybrid substratum offers one or more of the following advantages over the current 2D and 3D systems:

Compared with conventional 2D hepatocyte monolayer cultured on collagen-coated substratum, 3D hepatocyte monolayers cultured on a RGD/galactose hybrid substratum exhibited cellular structure and polarity, cell-cell interaction and differentiated functions similar to hepatocytes in vivo;

3D hepatocyte monolayer exhibited better attachment and mass transfer than 3D spheroids;

3D hepatocyte monolayer exhibited a more uniform monolayer morphology compared with the mixture of hepatocyte spheroids and monolayer on Primara dish [Tzanakakis E S et al. Cell Transplant. 2001; 10:329-42.];

3D hepatocyte monolayer exhibited a more effective mass transfer than the 'collagen-free' bioactive sandwich culture configuration;

The surface required to produce the 3D hepatocyte monolayer contains simple and quantitative controllable bioactive cues compared to a natural extracellular matrix which has unidentified components and batch-to-batch variation;

The synthetic polymer surface is chemically and mechanically stable for long-term storage and for cryopreservation;

Hepatocytes grown on the synthetic polymer surface may be cultured in normal culture medium without exposure to high levels of hormones compared to the highly functional monolayer cultured in Primara dishes which are maintained by high concentration of DEX;

The synthetic polymer surface is biocompatible and optically clear, which is ready to be adapted to the microplate-based ADME/TOX screening platform or a membrane-based bioreactor;

The same technology of conjugating multiple ligands onto PET film can be used to conjugate other bioactive ligands to better mimic basement membrane compositions for hepatocyte-based applications;

Applications

As described herein, the pre-spheroid 3D monolayer stage has been characterized with relatively strong cell-substratum interactions, enhanced cell-cell interactions, improved polarity and liver-specific functions than the conventional 2D monolayer which shows great potential for application. By stabilizing this configuration using a Galactose/RGD hybrid substratum, the present inventors were able to maintain this 3D monolayer stage up to one week. With its chemical and mechanical stability and quantitatively controllable bioactive cues, the transparent hybrid polymeric substratum is easily and readily incorporated into the current microplate-based automation platform for high-throughput drug metabolism/hepatotoxicity screening as an alternative for collagen-coated substratum. As exemplary drug hepatotoxicity study indicated, the 3D hepatocyte monolayer configuration provided improved in vitro prediction of the xenobiotics pharmaco-kinetics/dynamics data that better recapitulate the in vivo biological responses. This hybrid substratum may also be useful as a cell culture surface of a bioreactor for a bio-artificial liver device to obtain a 3D hepatocyte monolayer with better cell attachment and function.

With the effective adhesion of primary hepatocytes to the substratum and 3D cell characteristic, the prespheroid 3D hepatocyte monolayer stabilized on the RGD/galactose hybrid substratum can be useful in, but not limited to the following typical applications which are hepatocyte-based high throughput (i) xenobiotics metabolism or hepatotoxicity screening, (ii) drug studies, (iii) high-content screening and (iv) microplate based metabolism and toxic studies:

(i) Hepatocyte-based High Throughput Xenobiotics Metabolism or Hepatotoxicity Screening The 3D hepatocyte monolayers may be used for Hepatocyte-based high throughput xenobiotics metabolism or hepatotoxicity screening for example as described in [A P. Li Drug Discovery Today 2005; 2: 179-185; White R E. Annu Rev Pharmacol Toxicol. 2000; 40:133-57; Battersby B J. Trends Biotechnol. 2002; 20:167-73)

(ii) Drug Studies

ADME/TOX drug properties, namely, absorption, disposition, metabolism, elimination and toxicity, are important drug properties relevant to their critical for clinical success. The accurate prediction of drug ADME/T remains a major challenge for the pharmaceutical industry. The routine practice of preclinical and clinical drug ADME/T evaluation is apparently inadequate, as evidenced by the yearly withdrawal or severe use limitation of marketed drugs due to unexpected adverse effects. As the parenchymal cells of liver, the liver being the main organ of biotransformation and detoxification of xenobiotics including drugs, a hepatocyte based drug screening has been widely used to evaluate the metabolism and toxicity of the drug candidates. Most of the current hepatocyte-based high throughput metabolism/hepatotoxicity screenings of xenobiotics are done by using hepatocytes cultured on the collagen type I coated 96 well or 384 well microplates due to the easiness and consistency of the substrate preparation. Several other in vitro culture configuration have been tried to improve the functionality and biomimicry of the hepatocyte-based system, includes 3-D microcapsules, sandwich cultures, 3D spheroid culture micro-carrier culture, perfusion culture inside bioreactors and co-culture with non-parenchymal cells. However, those complex systems suffer from a technical complexity which is not easily adaptable to the standard high-throughput screening platforms, which provide automation and instrumentation which support parallel processes, such as plate-handling robots, high-density microplates and plate-scanning readers for the dye-based assays.

With its chemical and mechanical stability and quantitatively controllable bioactive cues, the transparent hybrid polymeric substratum provided herein for producing a 3D hepatocyte monolayer is easily and readily incorporated into the current microplate-based automation platform for high-throughput drug metabolism/hepatotoxicity screening as an alternative for collagen-coated substratum. The 3D hepatocyte monolayer configuration is anticipated to provide improved in vitro prediction of the xenobiotics pharmaco-kinetics/dynamics data that better recapitulates the in vivo biological responses.

Primary hepatocytes adhere effectively onto the transparent hybrid substratum in 96-well plates as a monolayer while exhibiting high levels of hepatocyte activities, cellular morphology and cell-cell interactions reminiscent of the cells in 3D spheroids. The hepatocytes cultured onto the hybrid substratum also exhibit high sensitivity to acetaminophen similar to the developing hepatocyte spheroids on galactosylated substratum. The monolayer of hepatocytes exhibiting the 3D cell behaviors on this flat hybrid substratum is compatible with any existing 2D cell culture platform well-established for high throughput xenobiotics screening or other applications.

(iii) High-content Screening

High-content screening is a high throughput approach applicable to cell-based systems that refers to the analysis of cellular assays using automated, image-based technology. This enables monitoring of multiple assay parameters, as well as capturing cellular information in one step—including cell shape and viability, target movement and interaction of the compound with other biomolecules. The difference is a few data points per well using a typical endpoint analysis versus thousands per well using a 2-D imager. Thus; a high-content approach can reduce the cost of cell-based screening because many cellular features can be tracked at once.

Due to the uniformity of the 3D hepatocyte monolayer maintained on the optically clear hybrid bioactive RGD/galactose substratum, the system may also be used as an alternative for collagen-coated substratum in the hepatocyte-based high content screening. This enables monitoring of multiple assay parameters (such as mitochondrial transmembrane potential, intracellular free calcium, plasma membrane integrity) in one step whilst elucidating cellular events and responses in the 3D hepatocyte monolayer which are indicative of hepatocytes in the liver.

(iv) Microplate Based Metabolism and Toxic Studies

The spheroid-mimetic properties, monolayer structure and effective attachment of the hepatocyte 3D monolayer cultured on hybrid substratum make the hybrid substratum as described herein a superior alternative for a conventional collagen-coated 2D substratum for hepatocyte-based applications such as microplate-based metabolism and hepatotoxicity testing and flat-plate bioartificial aided devices. As shown by the exemplary hepatotoxicity study of APAP, hepatocyte cultured on the hybridsubstratum showed more sensitivity towards APAP than hepatocytes cultured on collagen.

The higher sensitivity of hepatocytes cultured on PET-hybrid and on PET-Gal to acetaminophen(APAP)-induced hepatotoxicity might be caused by the higher cytochrome P450 (CYP45O) enzymatic activities. It is thought that the 'amplified effect of hepatotoxicity" of the co-administered inducer (3MC) might be due to the higher inducibility of CYP450 enzymes of hepatocytes cultured on PET-hybrid and PET-Gal.

EXAMPLES

Example 1

Identification and Characterisation of a Pre-spheroid 3D Hepatocyte Monolayer Stage on Galactosylated Substratum Example 1A Fabrication of PET Film Grafted with Acrylic Acid Biaxially oriented polyethylene terephthalate (PET) films of about 100 µm in thickness were purchased from Goodfellow Inc. of Cambridge, U.K. The galactose ligand, 1-O-(6'-aminohexyl)-D-galactopyranoside (AHG, M.W. 279) was synthesized according to the method developed previously [Ying et al, Biomacromolecules 2003, Jan.-Feb.; 4(1): 157-165; Findeis MA, Int J Pept Protein Res, 1994, May; 43(5):477-485; Weigel et al, Carbohydr Res, 1979; 70:83-91] and verified by NMR spectrum. RGD peptide (GRGDS; SEQ ID NO:3) was bought from Peptides International. All other chemicals were purchased from Sigma-Aldrich Singapore unless otherwise stated.

Polyacrylic acid (pAA) was grafted onto the PET film surface with a modified protocol [Ying et al, Biomacromolecules 2003, January-February; 4(1)157-165; Gupta et al, Biomaterials, 2002, February; 23(3):863-871] for conjugating bioactive ligands (FIG. 1). Briefly, PET film was cut into 2 cm×8 cm strips and cleaned in ethanol. The air-dried PET strips were subject to argon plasma treatment which was carried out in SAMCO Basic Plasma Kit (Samco International Inc.) operating at a radio frequency (RF) of 13.6 MHz. Argon was introduced into the chamber in the SAMCO kit at a flow rate of 50 ml/min with chamber pressure maintained at 20 Pa. Plasma was generated at an electric power of 40 W for 1 min. After the plasma treatment, the PET strips were exposed to atmosphere for 10 minutes to promote the formation of surface peroxides and hydroperoxides, which were used for the subsequent UV-induced grafting of pAA. For the UV-treatment, quartz tubes with length of 12 cm and diameter of 2.5 cm were used. The plasma-treated PET-strip was immersed in 30 ml of the aqueous solution containing acrylic acid in the quartz tube. Argon was bubbled through the solution to thoroughly remove oxygen and capped under Argon. The quartz tube was placed in water bath with constant temperature of 28° C. and then subjected to UV irradiation for 30 min using a 400 W flood lamp in UV-F 400 unit (Panacol-Elosol GmbH). After grafting, the PET strip was taken out of the tube and washed exhaustively with diionized water for 24 h to remove the residual homopolymer absorbed on the surface.

Example 1B

Fabrication and Characterization of Bioactive Substrata pAA-g-PET (i.e. PET grafted with pAA) strips were cut into circular disks with diameter of 6.4 mm in order to fit into the 96-well microplates. RGD peptide and galactose ligand (AHG) were conjugated via amide bonds onto the pAAc-g-PET substratum separately or simultaneously using a 'two steps' EDC (1-Ethyl-3-[3-dimethylaminopropyl]carbodiimide Hydrochloride) chemistry (FIG. 1). Briefly, at the first step, 100 μl of MES buffer (50 mM, pH of 5.5) containing 1.5 mg EDC and 0.3 mg sulfo-NHS were added to each 96-well containing the pAA-g-PET disk to activate the surface carboxylic groups by forming NHS esters. After 2 h activation at room temperature, the MES solution was completely removed and replenished with 100 μl phosphate buffer (0.1 M, pH of 7.4) containing ligands and allowed to react with activated substratum by shaking at 300 rpm in a thermomixer (Eppendorf) for 48 h at 4° C.

PET-RGD or PET-Gal was fabricated by reaction with RGD peptide (GRGDS; SEQ ID NO:3) or galactose ligand (1-O-(6'-aminohexyl)-D-galactopyranoside, AHG) respectively. The PET-Hybrid was fabricated by reaction with homogeneous mixture of GRGDS (SEQ ID NO:3) and AHG with different ratios.

After conjugation of the bioactive ligands, each sample was quenched with 0.5% ethanolamine solution for 1 to 5 minutes to block non-specific interactions due to the unreacted carboxylic groups with the hepatocytes. The microplates containing different substrata were sterilized by soaking with 70% ethanol for 3 h and then rinsed 3 times with PBS. Collagen-coated substratum was prepared by incubating 100 μl of 1.5 mg/ml collagen solution into each well of the 96-well microplates overnight at 4° C. The excess collagen solution was aspirated and each well rinsed 3 times with PBS.

The graft density of carboxylic groups on the PET films was determined by a colorimetric method using Toluidine Blue staining previously reported [Ying et al, Biomacromolecules 2003, January-February; 4(1)157-165; Uchida et al, Langmuir, 1993; 9:1221-1124].

XPS was used to qualitatively verify the pAA grafting and ligand conjugation onto the PET. Measurements were made on a VG ESCALAB Mk II spectrometer with a Mg Kα X-ray source (1253.6 eV photons) at a constant retard ratio of 40.

The XPS wide scan spectrum of the pristine PET film showed peaks corresponding to C 1s (binding energy, 285 eV) and 0 1s (binding energy, 532 eV), which revealed the presence of carbon and oxygen signals. The spectrum of PET-pAAc film (FIG. 2 top, left panel) showed the same peaks as pristine PET film; however, the relative intensity ratio of oxygen to carbon peaks is higher in PET-pAA film than in pristine PET film. The pAAc grafting density was quantified by TBO colorimetric assay [Ying et al, Biomacromolecules 2003, January-February; 4(1)157-165; Uchida et al, Langmuir, 1993; 9:1221-1124]. PET-pAA substrata with carboxyl group densities from 8.2±2.3 to 258.2±24.2 nmol/cm$^2$ could be obtained by varying the initial concentration of the acrylic acid monomer solution from 1%-5%.

The difference in density of carboxylic groups and conjugated galactose ligands was not expected to lead to significant differences in hepatocytes 3D spheroids formation and functional maintenance when the densities went above certain value [see Ying et al, Biomacromolecules 2003]. 3.75% acrylic acid monomer solution was chosen to fabricate PET-pAA with carboxyl group density of 78.5±10.2 nmol/cm$^2$ for the following ligands conjugation and cell culture work in order to achieve reasonably high ligand conjugation density using the relatively inefficient two-step 'EDC chemistry' [Hersel et al, Biomaterials, 2003, November; 24(24):4385-4415].

Figure 2:
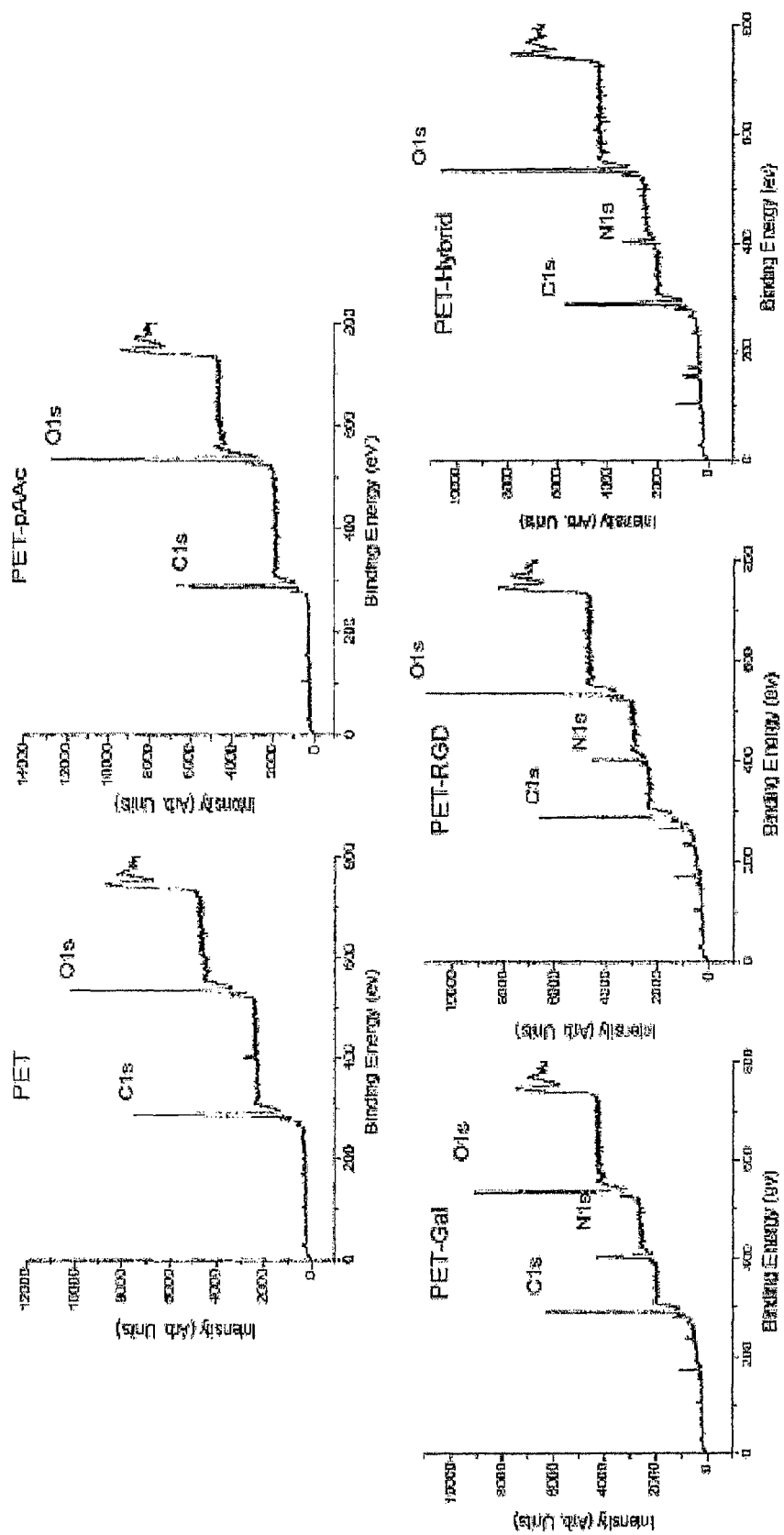
FIG. 2. XPS wide scanning spectra of PET, PET-g-AA, PET-gal and PET-RGD which showed the successful grafting of acrylic acids and following conjugation of RGD and Gal ligands onto the PET film.
Figure 3A:
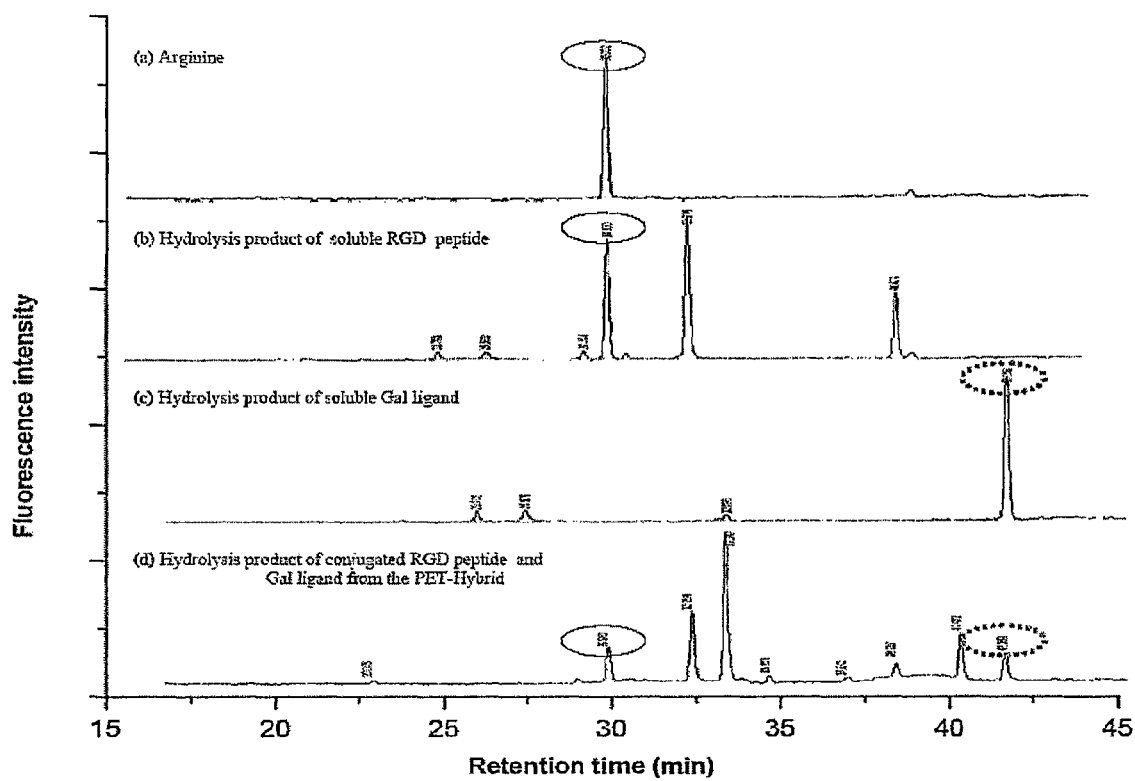
FIG. 3. Graphs illustrating quantitative analysis of the conjugated RGD peptide (GRGDS; SEQ ID NO:3) and Gal ligand (1-O-(6'-aminohexyl)-D-galactopyranoside; AHG) by RP-FIPLC: (A) Representative RP-HPLC Chromatograms of Arginine (a); hydrolysis products of soluble RGD peptide (b) and Gal ligand (c); hydrolysis product of the PET-hybrid (d); (B) Conjugation efficiency curve of RGD peptide onto the PETpAAc; (C) Conjugation efficiency curve of galactose ligand onto the pAAc-PET substratum.

RGD peptide (GRGDS; SEQ ID NO:3) and/or Gal ligand (AHG) were conjugated onto the PET-pAA film (FIG. 1), and successful conjugation of ligands was confirmed by XPS (FIG. 2). In contrast to pristine PET and PET-pAA, a new peak corresponding to N 1s (binding energy, 400eV) appeared in the spectra of the PET-RGD, PET-Gal and PET-Hybrid films. To measure the amount of the GRGDS (SEQ ID NO:3) and/or AHG conjugated onto the films, the conjugated GRGDS (SEQ ID NO:3) and/or AHG was removed from the film by acid hydrolysis, and the hydrolyzed GRGDS (SEQ ID NO:3) and AHG fed quantified by RP-HPLC with a fluorescence detector after derivatizing the α-amine on the hydrolyzed GRGDS (SEQ ID NO:3) and AHG to fluorescent substances. Representative chromatograms of different samples are illustrated in FIG. 3A. The ratio of the GRGDS (SEQ ID NO:3) and AHG in the PET-Hybrid was controlled by monitoring the conjugation efficiencies of the GRGDS (SEQ ID NO:3) and AHG on the film.

RGD and/or Gal ligands on PET were hydrolyzed off the substrata using Acid Hydrolysis Station (C.A.T. GmbH & Co.) in 6N HCl at 110° C. for 24 h under vacuum. The cooled hydrolyzed solution was filtered into a new vial and evaporated under nitrogen. The hydrolyzed ligands from PET were re-suspended in 50 µl diionized-water and derivatized using ATTO-TAG™ CBQCA Amine-Derivatization Kit (Molecular Probes) for fluorescence detection after separation on a reverse phase C-18 column in HPLC (Agilent Technology). Optimized operational conditions: mobile phase: A: Water+0.1% TFA, B: Acetonitrile+0.1% TFA; Gradient: A/B (98:2) to (70:30) in 45 min; Flow rate: 1 ml/min; Fluorescence detection: excitation at 450 nm, emission at 550 nm. Standard curves were established against soluble RGD peptide and Gal ligand. Among the hydrolysis products of RGD peptide, the peak corresponding to arginine was chosen to represent and quantify RGD peptide due to its sharpness and early elution time in the chromatograph.

Figure 3B:
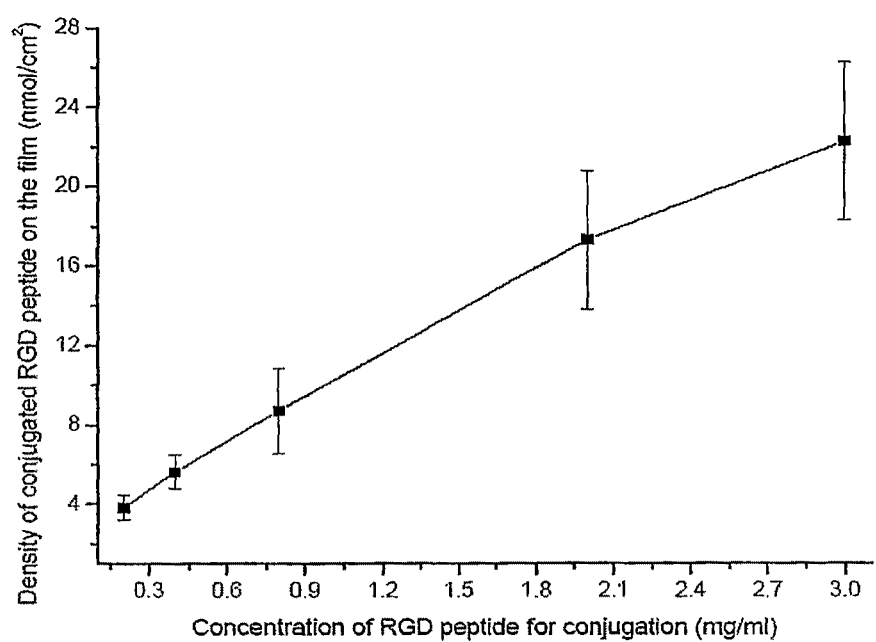
Figure 3C:
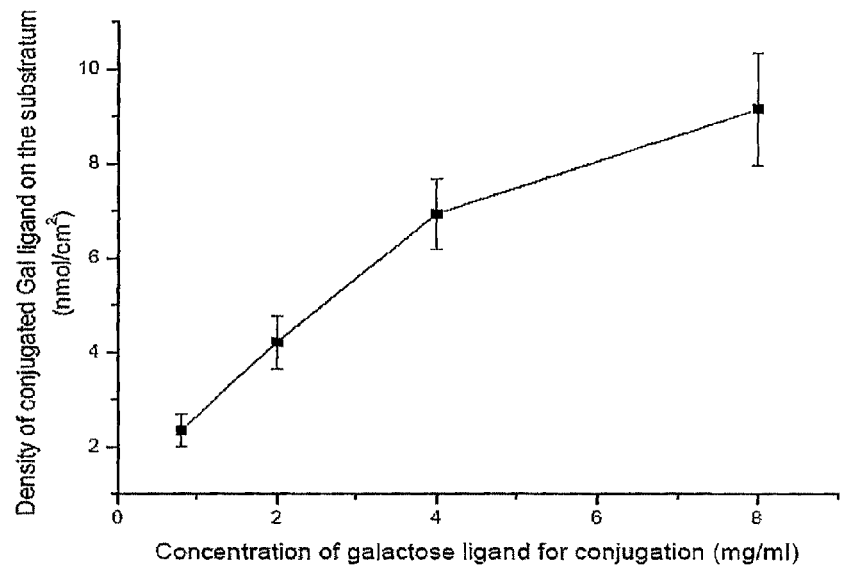

GRGDS (SEQ ID NO:3) exhibited higher conjugation efficiency than AHG (FIG. 3B). For 3 mg/mi (0.3 mg per 96 well) of AHG, 0.6 mg (0.06 mg per 96 well) of GRGDS (SEQ ID NO:3) reacted with the activated PET-pAAc film to achieve a conjugation ratio of ~1:1. The final density of the conjugated GRGDS (SEQ ID NO:3) and AHG on the film was $5.63 \pm 0.86$ nmol/cm$^2$ and $6.94 \pm 0.74$ nmol/cm$^2$ respectively. For $78.5 \pm 10.2$ nmol/cm$^2$ of carboxylic groups available on the PET-pAAc film, about 16% were conjugated with the ligands. To achieve 1:5 and 5:1 ratios of conjugated GRGDS (SEQ ID NO:3) and AHG, 0.12 mg/ml and 3 mg/ml GRGDS (SEQ ID NO:3) respectively were used to conjugate with 3 mg/ml AHG onto the PET-pAA film. The final densities of GRGDS/AHG were $19.40 \pm 3.19/4.36 \pm 0.45$ nmol/cm$^2$ and $1.31 \pm 0.49/5.38 \pm 0.89$ nmol/cm$^2$. For PET-Gal and PET-RGD films, 3 mg/ml AHG and 0.6 mg/ml GRGDS (SEQ ID NO:3) were conjugated to the PET-pAA film respectively. The final density of AHG of PET-Gal is $5.92 \pm 0.74$ nmol/cm$^2$ and GRGDS (SEQ ID NO:3) of PET-RGD is $7.04 \pm 0.96$ nmol/cm$^2$.

Example 1C

Dynamic Process of Hepatocyte Self-assembly on Galactosylated Substratum

The process of hepatocyte self-assembly on galactosylated substratum was investigated by using the following methods.

A 'Galactosylated-bottom' culture dish was assembled by using a WillCo-dish Kit (WillCo Wells B.V., Netherland) with the galactosylated PET film (as shown in Example 1B) glued to a special dish with the central region of the bottom empty. The special dish used was a 35 mm dish. Hepatocytes were seeded onto the galactosylated film at a density of $1 \times 10^5$ cells/cm$^2$ and cultured in a live imaging chamber with temperature and CO$_2$ control (Carl Zeiss). Transmission images of hepatocyte morphology were captured every 5 min using 10× objective of Zeiss Meta 510 confocal microscopy for up to 3 days. The dynamic change of cell morphology in terms of the spreading tendency was quantified as the total area of the substratum covered by cells by image processing (Imaging Process Probe) and expressed as substratum coverage calculated by normalization with the area of the post-seeding cells at 0 h.

3.7% paraformaldehyde-fixed samples were rinsed in PBS and then post-fixed with osmium tetroxide for 1 h. Dehydration was accomplished using a graded series of ethanol (25%, 50%, 75%, 95%, and 100%). The samples were then critical point dried for 2 h in absolute alcohol, mounted onto a brass stub and sputter-coated with platinum (JFC-1600, JEOL), before being viewed under a field emission scanning electron microscope (JSM-7400F, JEOL).

Figure 4A:
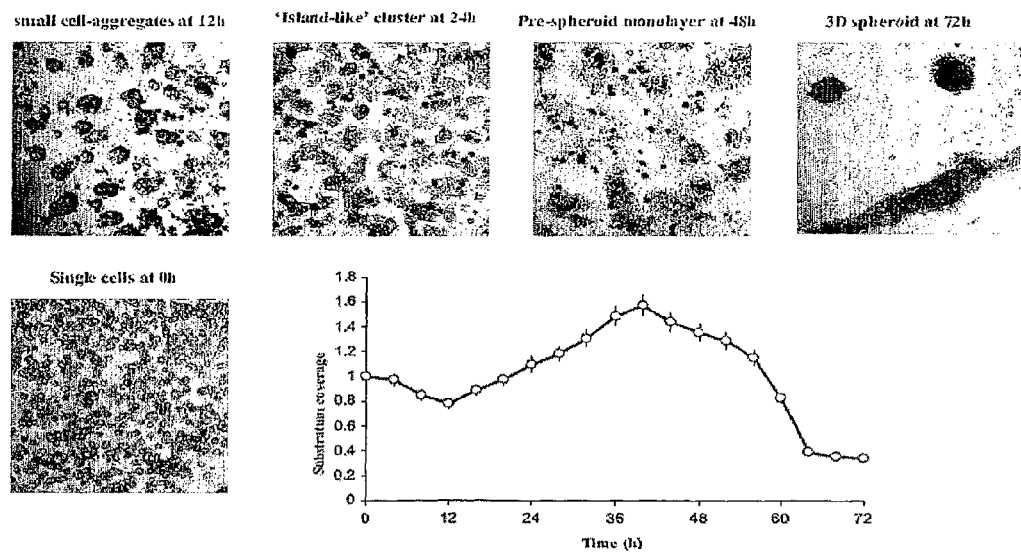
FIG. 4. Microscopy showing morphology of hepatocyte cultured on the galactosylated substratum at different stages during hepatocyte spheroid formation (A) phase contrast images and substratum coverage (B) Scanning Electron Microscopy images FIG. 5. F-Actin reorganization at various time points during hepatocyte 3D spheroid formation on the galactosylated substratum (upper panel) and conventional 2D monolayer formation on the collagen-coated substratum (lower panel)
Figure 4B:
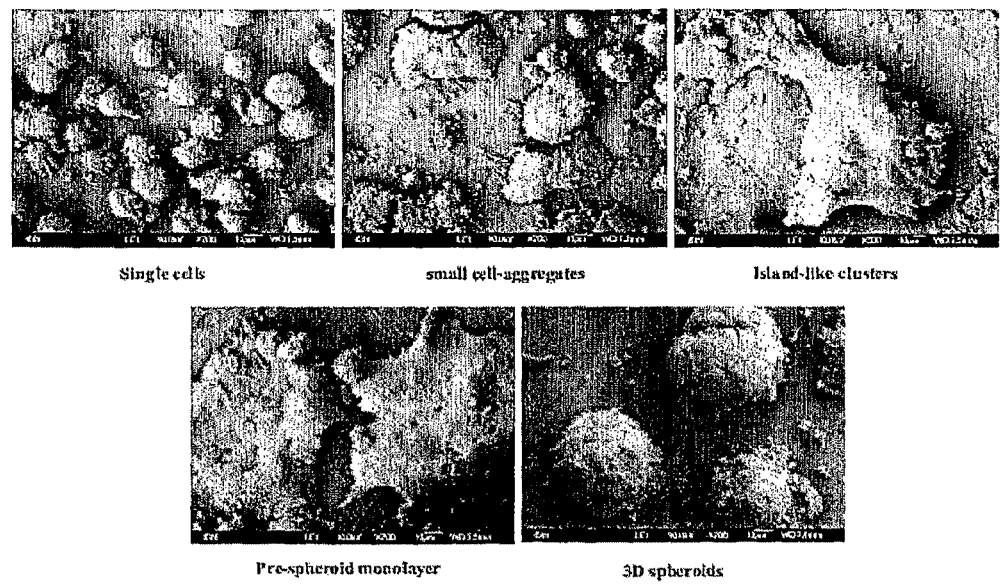

During hepatocyte self-assembly, dramatic changes occurred in cell morphology and substratum coverage as shown by confocal transmission images (FIG. 4A) and SEM images (FIG. 4B). Hepatocytes on galactosylated substratum underwent 2 cycles of cell-aggregation to form mature spheroids. Single hepatocytes seeded on this galactosylated substratum first formed small aggregates containing several hepatocytes within 12 h with reduced area coverage of the substratum. Migration of the cells facilitated the establishment of cell-cell contacts and contractions among small aggregates which gradually merged into larger 'island-like' clusters after 1 day. The island-like clusters underwent further spreading to form monolayers with the maximum substratum coverage within 2 days. Due to the strong cell-cell contraction, the cells at the edge of the pre-spheroid monolayer were stretched to fold into multilayers and compacted into mature and larger 3D spheroids which finally detached from the substratum after 3 days.

Example 1D

Cytoskeleton Reorganization During Hepatocyte Spheroid Self-assembly

Since the cytoskeleton is a major force apparatus which mediates cell spreading, migration and tissue formation, the dynamic organization of actin filaments, one of the main cytoskeletal proteins was investigated during hepatocyte 3D spheroid self-assembly on the galactosylated substratum and during conventional 2D monolayer formation on a collagen-coated substratum as comparison.

For F-actin staining, the cells were fixed using 3.7% paraformaldehyde, blocked in 10% fetal calf serum (FCS) at room temperature for 1 h, permeabilized for 5 min in 0.1% Triton X-100 plus 1% bovine serum albumin (BSA), incubated with TRITC-phalloidin (1 µg/ml) for 20 min and then rinsed three times before imaging. For staining of p-FAK, E-cadherin and double staining of MRP2/CD147 and ZO-1/CD147, 3.7% paraformaldehyde-fixed cells were blocked in 10% FCS at room temperature for 1 h. Samples were incubated with the primary antibodies (1:10 for ZO-1/CD147 and MRP2/CD147 double staining; 1:20 for E-cadherin and p-FAK staining Primary rabbit anti-p-FAK antibody was purchased from Upstate (Charlottesville, USA); Primary rabbit anti-E-Cadherin antibody was purchased from Santa Cruz (CA, USA) overnight at 4° C., before being rinsed 3× with PBS. Samples were then incubated with the secondary antibodies. Secondary TRITC-conjugated goat anti-rabbit IgG and FITC-conjugated goat anti-mouse IgG were purchased from Molecular Probes (Invitrogen, Singapore) at room temperature for 1 h and rinsed 3× with PBS before being mounted with Fluor Save™ (Calbiochem, San Diego, Calif.). The samples were viewed with a confocal microscope (Fluoview 300, Olympus) using 63× water lens.

Figure 5:
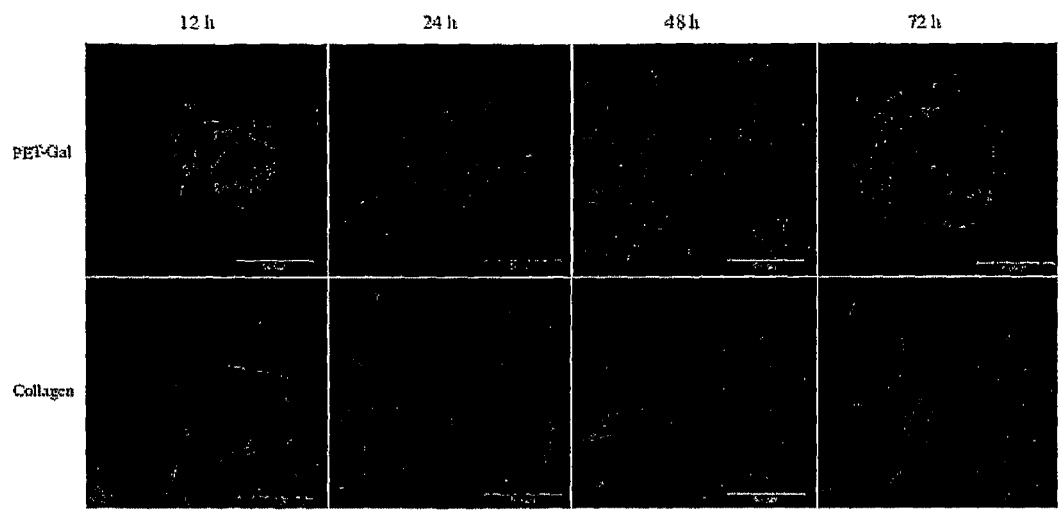

Actin filaments underwent significant rearrangement during the multi-staged 3D spheroid formation. For hepatocytes in small-aggregates 12 h after seeding, actin filaments were already localized to the cell-cell contact regions (FIG. 5) indicating establishment of cell-cell interaction. When small hepatocyte aggregates merged into 'island-like' clusters after 1 day, actin stress fibers were observed throughout the cell-substratum contact regions. These gradually re-localized back to the cell periphery as clusters which spread and formed pre-spheroid monolayers until observed actin stress fibers were significantly reduced and only seen in cells at the edge of the monolayer. The cortical distribution of actin filaments at the cell-cell contact region of the pre-spheroid monolayer was also observed in the mature 3D spheroids indicating the 3D cell characteristic of the pre-spheroid monolayer. In contrast, actin filaments gradually formed stress fibers which increased in intensity throughout the cell-substratum contact region during conventional 2D monolayer formation in the collagen-coated substratum (FIG. 5).

Example 1E

Figure 6A:
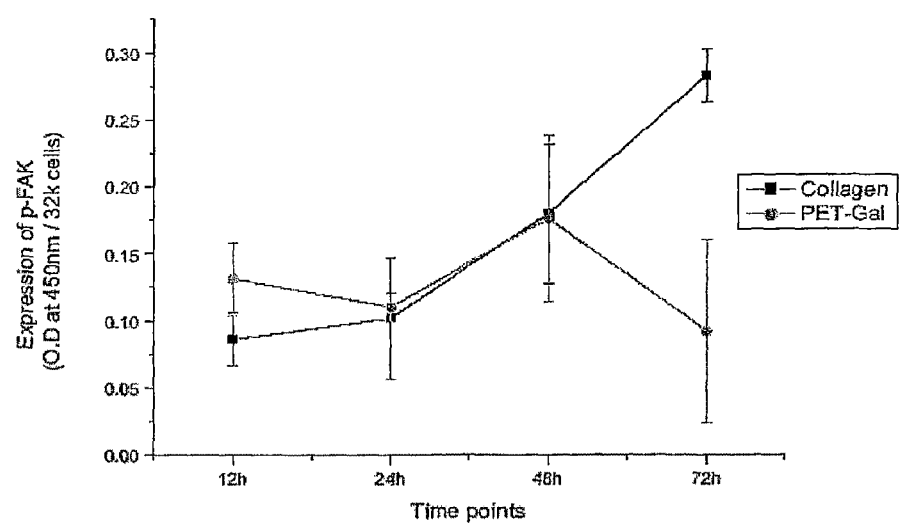
FIG. 6. p-FAK and E-cadherin expression and distribution during hepatocyte 3D spheroids formation. (A) Dynamic changes of p-FAK expression quantified by ELISA during 3 d spheroids and 2D monolayer formation; (B) Western blot analysis of E-Cadherin and β-actin expression; GAPDH was used as loading control. (C) p-FAK/E-Cadherin double staining of conventional 2D monolayer, pre-spheroid 3D monolayer, 3D spheroid.

Regulation of Hepatocyte Self-assembly by the Balance of Cell-cell and Cell-substratum Interaction Since the actin cytoskeleton is linked to both focal adhesion complexes to mediate cell-substratum interaction via adaptor proteins ($\alpha$-actinin, talin, filamin) and to cadherins to mediate the cell-cell interactions via catenin, the presence of different actin configurations is indicative of the competition between forces exerted by cell-cell and cell-substratum interaction. This competition was examined by quantifying (by ELISA) the expression level changes of phosphorylated Focal Adhesion Kinase (p-FAK) and E-Cadherin (by ELISA) during the formation of a hepatocyte 3D monolayer and a conventional 2D monolayer (FIG. 6A). Focal adhesion kinase (FAK) is a key protein involved in modulating assembly of focal adhesions in response to force exerted by the cytoskeleton on attachments to the substratum via integrins. Integrin-mediated adhesion of cells to the extracellular matrix (ECM) triggers autophosphorylation at the Tyr-397 residue of FAK. Expression of p-FAK was quantified as the indicator of cell-substratum interaction. As the main cellular adhesion protein to mediate the cell-cell interaction, E-Cadherin was chosen as the indicator of cell-cell interaction.

ELISA of p-FAK was performed according to the protocol of FACE™ p-FAK ELISA kit (Active Motif, Inc., USA). Briefly, hepatocytes cultured on different substrata in 96-well plates were fixed with 3.7% paraformaldehyde for 20 min at room temperature for ELISA of p-FAK or fixed with a methanol/acetone (1:1) solution for 15 min. After rinsing with 0.1% Triton-X 100 and blocked with 1% BSA for 1 h at room temperature, the cells were incubated with 1:200 diluted anti-p-FAK primary antibody overnight at 4° C. The cells were washed for 3 times with 0.1% Triton-X 100 and incubated with 1:2500 diluted anti-IgM-HRP (horseradish peroxidase) secondary antibody for 1 h at room temperature. After 3× rinsing with 0.1% Triton-X 100 and 2× rinsing with PBS, the HRP activity was colorimetrically measured by developing with 100 µl/well TMB (Tetramethyl benzidine, BETHYL Laboratories) substrate solution. Absorption was measured at 450 nm.

For Western Blotting studies, cultured hepatocytes were lysed with RIPA buffer (50 mm Tris-HCL, 150 mM NaCl, 1% NP-40, 0.5% sodium deoxycholate, 0.1% SDS) supplemented with protease inhibitor cocktail (Roche, Singapore) for 30 min at 4° C. Lysates then were clarified by centrifugation at 10,000 g for 20 min at 4° C. The protein concentration per sample was quantified by $D_c$ protein Reagent assay (Bio-rad, U.S) which was diluted in sample loading buffer (2% SDS, 80 mM Tris-HCl, 10% glycerol, 0.1% Bromophenol blue, 5% 2-mercaptoethanol) and heated for 5 min at 95° C. 10 µg protein sample per lane was loaded and fractionated by 7.5% SDS-PAGE gel and transferred to a PVDF membrane (Millipore, U.S) by semi-dry electroblotting. The membranes were blocked with 5% non-fat milk in TBS-T for 1 h at room temperature and incubated with primary rabbit anti-E-Cadherin or anti-$\beta$-actin or anti-GAPDH (1:1000 diluted in TBS-T buffer) overnight at 4° C. After 3× washing with TBS-T buffer, the membrane was incubated with secondary donkey peroxidase-conjugated anti-rabbit IgG 1:10,000 diluted in 2.5% non-fat milk for 1 h at room temperature. After 4× washing with TBS-T buffer, the membrane was treated with Amersham ELC plus reagent (GE Healthcare, UK); and light emission was detected by exposing the membrane to a Hyperfilm (GE Healthcare, UK). Films were developed by using a KODAK Medical X-ray Processor (KODAK, USA) and imaged by using a KODAK IMAGE Station 2000MM (KODAK, USA).

During the process of hepatocyte spheroid self-assembly, p-FAK expression level initially increased with the formation of pre-spheroid monolayer, but then fell with the formation of 3D mature spheroids. In contrast, a constant increase of p-FAK expression was observed during the conventional 2D monolayer formation.

Figure 6B:
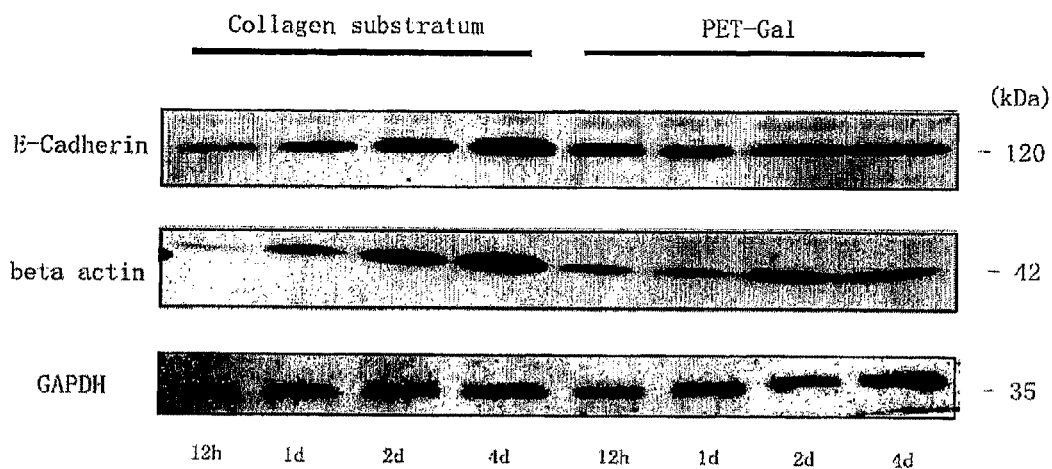
Figure 6:
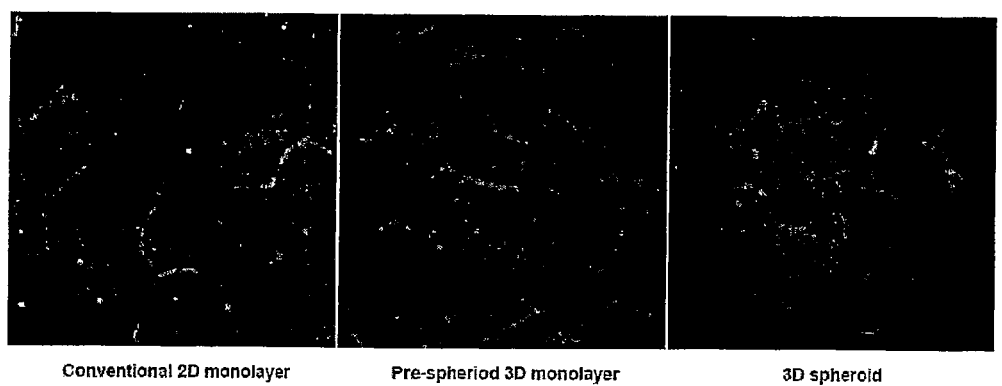

E-cadherin was highly expressed in hepatocytes at all 4 stages cultured on the PET-gal film, with a slight up-regulation in cells from the pre-spheroid monolayer and 3D spheroids (FIG. 6B), indicating strong cell-cell interactions. The expression of E-cadherin in hepatocytes cultured on collagen substratum was initially rare, and subsequently significantly up-regulated during 2D hepatocyte monolayer formation (FIG. 6B), indicating gradual enhancement of cell-cell interactions.

The observation of cytoskeletons organization and p-FAK/E-Cadherin expression indicated that among the four stages of hepatocyte spheroid formation, the pre-spheroid monolayer exhibited a similar actin distribution and E-Cadherin expression level to 3D spheroids, but with stronger p-FAK expression than 3D spheroid. Double-immunoassaying of E-Cadherin/p-FAK of the pre-spheroid monolayer, 3D spheroid and conventional 2D monolayer confirmed the ELISA results (FIG. 6C). E-Cadherin localized at the lateral borders of the pre-spheroid 3D monolayer and in 3D spheroids, which is much less than in 2D monolayer. p-FAK clusters were observed in 2D monolayer and at lower levels in pre-spheroid 3D monolayers, and were not seen in 3D spheroids. All the above findings indicate that the pre-spheroid monolayer is a superior configuration for hepatocyte-based applications.

Example 1F

Hepatocyte Polarity and Tight-junction Formation in Pre-spheroid 3D Monolayers, 3D Spheroids and Conventional Monolayers The functional structure features among different culture configurations were evaluated by polarity and tight junction formation, which are valuable criteria for in vitro configurations if they are to predict the in vivo situation. Studies of the formation of cellular polarity was undertaken by investigating the bile canalicular transporter, the multidrug resistance-associated protein (Mrp2) and the basolateral CD147 as apical and basolateral markers respectively. Confocal images were processed to quantify the co-localization of these two markers. Primary anti-CD147 monoclonal antibody was purchased from Serotec (Raleigh, N.C.). Primary rabbit anti-ZO-1 antibody was purchased from Zymed laboratories (San Francisco, USA).

Besides the fluorescence double-staining, quantification of the Mrp2 or ZO-1 localization along the cell boundaries (basolateral CD147) was performed by implementing an image processing algorithm developed in Visual C++ 6.0. The green pixels in each image from the CD147 staining were first binarized by thresholding segmentation to yield cell boundaries with one-pixel thickness; the red pixels in the same image from the Mrp2 or ZO-1 staining were binarized to yield the regions that contain a significant concentration of the respective marker; and the total number of red pixels in the image was calculated as $I_{total}$. For each red pixel, the distance to the closest cell boundary pixel was obtained from a distance map (Ling et al., Information Processing Letters 51, 1994). Extra-cellular red pixels residing in the bile canaliculi-like structures were identified and differentiated from the intra-cellular red pixels by using the 'region growing' algorithm (Bischof et al., IEEE Transactions on Pattern Analysis and Machine Intelligence 1994). Intra-cellular red pixels within 2-pixel distance from the closest boundary pixel and extracellular red pixels were counted as $I_{localized}$. The ratio between $I_{localized}$ and $I_{total}$ was used to describe the localization of Mrp2 or ZO-1 along the cell boundary.

Figure 7A:
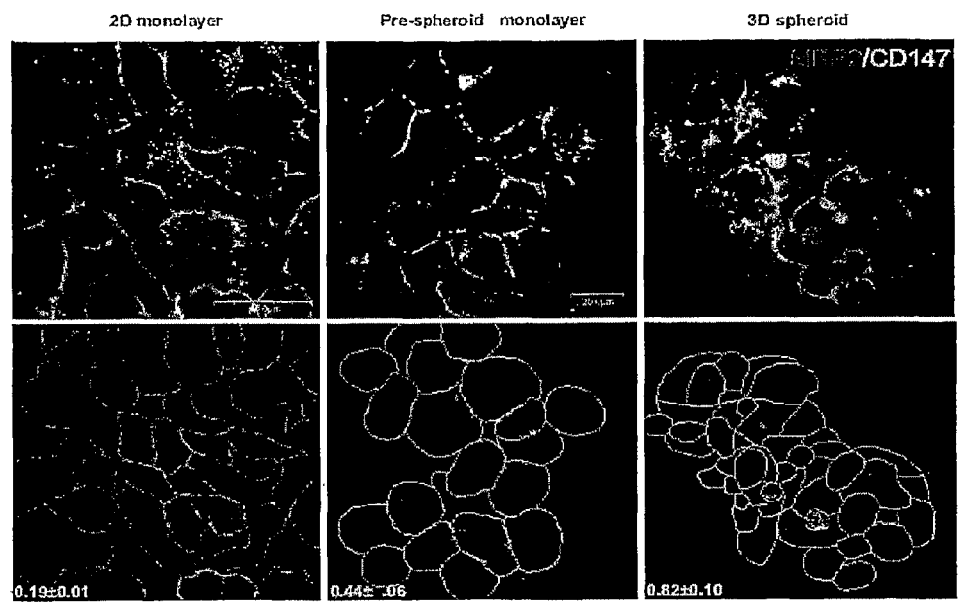
FIG. 7. The polarity and tight junction formation of hepatocytes in conventional 2D monolayer; pre-spheroid 3D monolayer, 3D spheroid (A) double-staining of bile canalicular transporter MRP2 and basolateral marker CD143 (B) double-staining of tight junction protein ZO-1 and basolateral marker CD143. The images were processed and the number in the corner of each processed image is a quantitative measure of the Mrp2 or ZO-1 localization along the cell boundaries as polarity marker, by an algorithm described in the materials and methods.
Figure 7B:
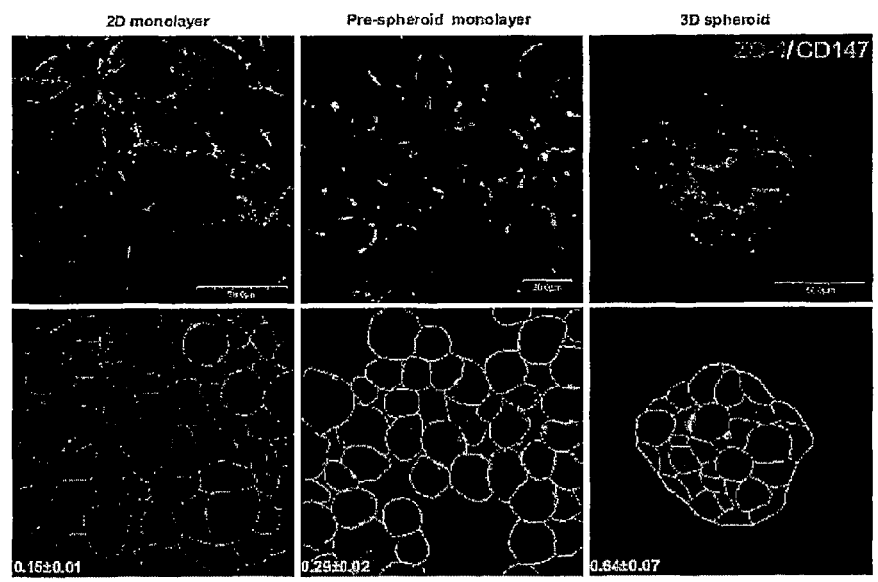

Random distribution of Mrp2 inside the cell bodies was observed in the conventional 2D monolayer on collagen, while in pre-spheroid 3D monolayers, Mrp2 localized to the cell-cell contact regions, which is one of the later events in the process of polarity establishment. In 3D spheroids, polarity structure was fully built, with more Mrp2 filling up the bile canaliculi-like structures established among several contacted cells. Tight junction staining using tight junction protein ZO-1 and basolateral markers CD147 showed the same trend. In pre-spheroid 3D monolayers, the tight junction protein ZO-1 became concentrated in localized regions along cell-cell contacts, whereas in conventional 2D monolayers, ZO-1 was more diffuse (FIGS. 7A and B).

Example 1G

Differentiated Functions of Pre-spheroid 3D Monolayers, 3D Spheroids and Conventional Monolayers To evaluate the potential application potential of the pre-spheroid 3D monolayer configuration, liver-specific functions such as synthetic, detoxifying and metabolic activities of hepatocytes in this transient stage cultured at day 2 were compared with conventional 2D monolayers at day 2, as well as with 3D spheroids at Day 3.

All functional data was normalized to $10^6$ cells. Cell number was calculated based on the total DNA amount using Pico-green DNA quantification kits (Invitrogen). The daily albumin production was measured using the Rat Albumin ELISA Quantitation Kit (Bethyl Laboratories Inc., Montgomery, Tex.). The urea production of the hepatocyte cultures incubated in culture medium with 2 mM $NH_4Cl$ for 90 min was measured using the Urea Nitrogen Kit (Stanbio Laboratory, Boerne, Tex.). The 7-ethoxyresorufin-O-deethylation (EROD) assay, which is a measure of the de-ethylation activity of cytochrome P450 (CYP) 1A-associated monooxygenase enzymes, was initiated by incubating the cultures with 39.2 µM 7-ethoxyresorufin in culture medium at 37° C. for 4 h, both with and without the induction by 3-MC one day earlier before measurement. The amount of resorufin converted by the enzymes was calculated by measuring the resorufin fluorescence in the incubation medium at 543 nm excitation/570 nm emission against resorufin standards using the microplate reader (Tecan Trading AG, Switzerland).

Figure 8:
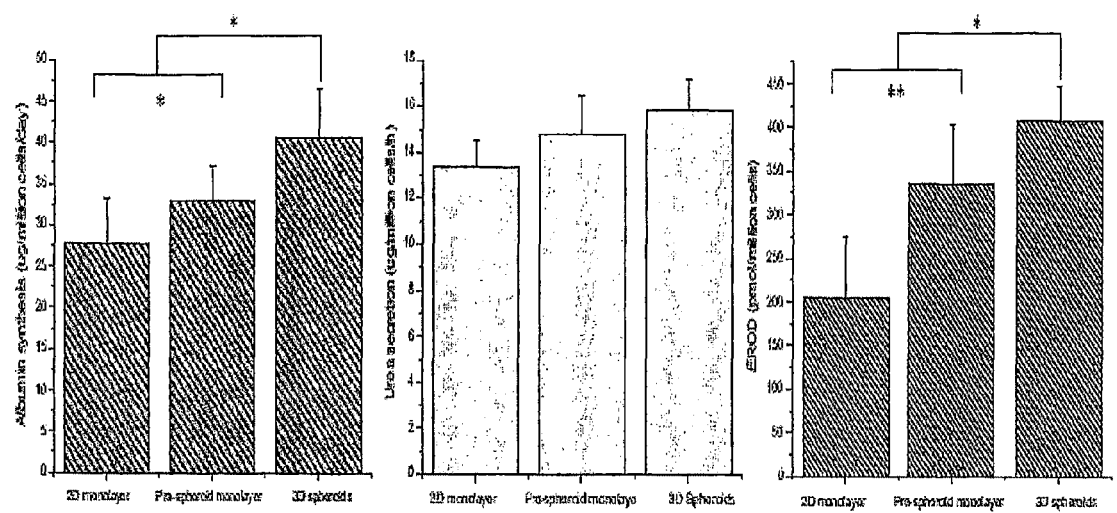
FIG. 8. Liver-specific functions hepatocytes in conventional 2D monolayer, pre-spheroid 3D monolayer, 3D spheroid. (A) Albumin secretion; (B) urea production; (C) 7-ethoxyresorufin-O-deethylase (EROD) cytochrome P450 activity.

FIG. 8 shows that the albumin secretion and 7-ethoxyresorufin-O-deethylation cytochrome P450 activity induced by 3MC of hepatocytes as pre-spheroid 3D monolayers was significantly higher than that of conventional 2D monolayers and comparable to that of 3D spheroids. Urea synthesis did not show significant difference amongst these three configurations.

Example 1H

Sensitivity of Pre-spheroid 3D Monolayers and Conventional Monolayers to Acetaminophen-induced Hepatotoxicity Acetaminophen (APAP), a commonly used analgesic, is known to cause hepatotoxicity when ingested in large quantities in both animals and man, especially when administered after chronic ethanol consumption. Hepatotoxicity stems from acetaminophen biotransformation by cytochrome P450 (P450) enzymes to a toxic intermediate which can bind to tissue macromolecules, there by initiating cellular necrosis. CYP1A, CYP2E and CYP3A are the most active isoforms which have been shown to be able to metabolize acetaminophen. The induction of CYP activities had been shown to result in an increased APAP toxicity. Aflatoxin B1 causes acute hepatotoxicity and liver carcinomas in humans and laboratory animals. Aflatoxin is normally oxidized by CYP2C11 and 3A2 to form an intermediate reactive epoxide, which binds to cellular macromolecules and causes injury to periportal regions of the liver. Responses to hepatotoxicity caused by acetaminophen or aflatoxin B1 to the prespheroid monolayer and the 2D monolayer were investigated.

The hepatotoxicity testing, acetaminophen (APAP) was dissolved in DMSO so that the final concentration of DMSO in the medium was less than 0.2% at every drug concentration. Pre-spheroid 3D hepatocyte monolayer cultured on PET-Gal films at Day 2 and conventional hepatocytes cultured on collagen at Day 2 were exposed to APAP at a variety of various concentrations for 24 h, at which timel cell viability was measured.

The reduction of the water-soluble tetrazolium salts MTS (3-[4,5,dimethylthiazol-2-yl]-5-[3-carboxymethoxy-phenyl]-2-[4-sulfophenyl]-2H tetrazolium, inner salt) was used to quantify cell viability, and was measured using the CellTiter 96 Aqueous One Solution Reagent (Promega). After treatment with test toxin, cells were exposed to 100 µl/well of 5× diluted MTS reagent in phenol-red-free William's E culture medium and incubated for 3 h at 37° C. The absorption of MTS was measured at 450 nm using microplate reader (Tecan Safire²). The response of APAP-induced hepatotoxicity of hepatocytes cultured on different substrata was expressed as the 'survival ratio', which was calculated by the MTS value on APAP-induced hepatocytes normalized to the MTS data on hepatocytes not exposed to APAP.

Figure 9:
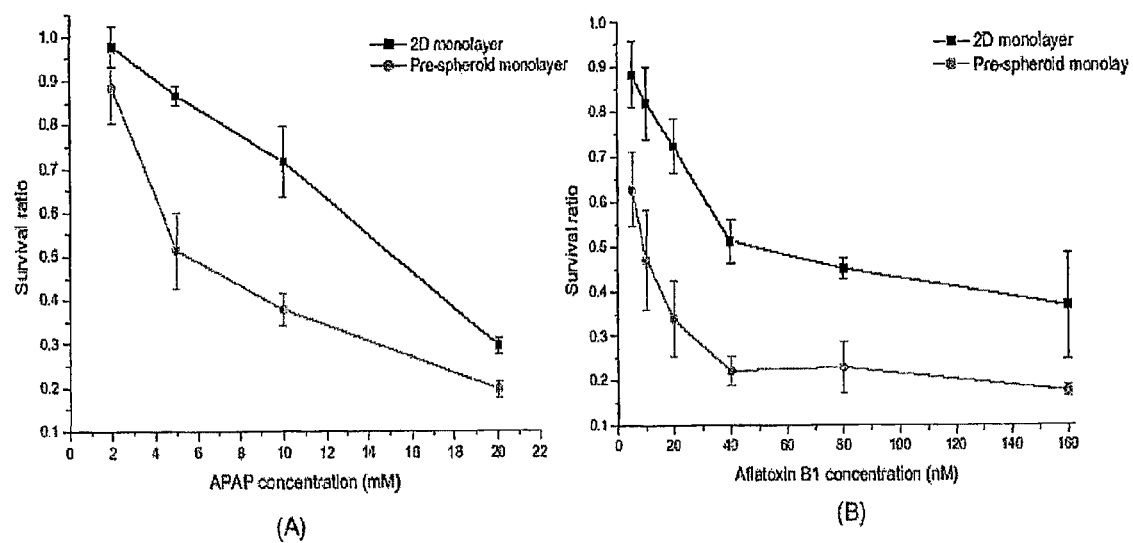
FIG. 9. Hepatotoxic sensitivity induced by (A) acetaminophen and (B) Aflatoxin B1 of hepatocytes in the 2D monolayer and the pre-spheroid monolayer.

Under drug-free conditions, hepatocytes in all culture configurations showed similar basal levels of viability. At all drug dosages, the prespheroid monolayers exhibited higher sensitivity (as determined by a lower survival ratio) to acetaminophen or aflatoxin B1-induced hepatotoxicity than the 2D monolayers (FIG. 9). Higher sensitivity to acetaminophen or aflatoxin-induced hepatotoxicity was also seen in 3D spheroids compared to 2D monolayers (data not shown), indicating the drug response of the prespheroid monolayer mimicked the response of the 3D spheroids.

Example 2

Stabilizing the 3D Hepatocyte Monolayer on Hybrid RGD/Galactose Substratum

Since the pre-spheroid 3D monolayer identified in example 1 is only a transient stage during the dynamic process of hepatocyte self-assembly, the inventors investigated the feasibility of stabilizing the pre-spheroids 3D monolayers, so that they could be used in long-term applications; by conjugating GRGDS peptide and galactose ligand onto a PET substratum (RGD/galactose PET-Hybrid). The methods to fabricate different bioactive substrata (PET-Gal, PET-RGD, PET-Hybrid) have been described in Example 1B.

Example 2A

Hepatocyte Attachment on Bioactive Substrata

Hepatocyte attachment on different bioactive substrata (PET-Gal, PET-RGD, PET-Hybrid) was investigated.

Initially, hepatocytes were harvested from male Wistar rats weighing 250-300 g by a two-step in situ collagenase perfusion method [Seglen et al., Methods Cell Biol 1976; 13:29-83]. Viability of the hepatocytes was determined to be >90% by Trypan Blue exclusion assay and a yield of >$10^8$ cells/rat.

Freshly isolated rat hepatocytes ($3.2 \times 10^4$) were seeded onto different substrata at $1 \times 10^5$ cells/cm$^2$ within 96-well microplate and cultured in 100 µl of William's E culture medium supplemented with 10 mM $NaHCO_3$, 1 mg/ml BSA, 10 ng/ml of epithelial growth factor (EGF), 0.5 µg/ml of insulin, 5 nM dexamethasone, 50 ng/ml linoleic acid, 100 units/ml penicillin, and 100 µg/ml streptomycin. Cells were incubated with 5% $CO_2$ at 37° C. and 95% humidity. After 2 h incubation, culture medium containing the unattached cells was removed; the wells were rinsed with PBS and replenished with fresh culture medium. Initial culture of hepatocytes were incubated for 2 hrs and unattached cells were removed.

Hepatocyte attachment on different substrata after 2 h, that being after the unattached cells were removed, was calculated based on a DNA analysis method [Brunk et al., Anal Biochem, 1979, Jan. 15; 92(2):497-500]. Attached cells were lysed on the substrata by a freeze-thaw cycle by freezing in DNA-free DI-water at −80° C. overnight and thaw at 37° C. DNA concentration was determined using PicoGreen® dsDNA quantitation kit (Molecular Probe). The attached cell number was determined using a standard curve generated from the DNA concentrations of known number of cells. Hepatocyte attachment on different substrata was expressed as the seeding efficiency (attached cell number divided by total cell number initially seeded).

Figure 10A:
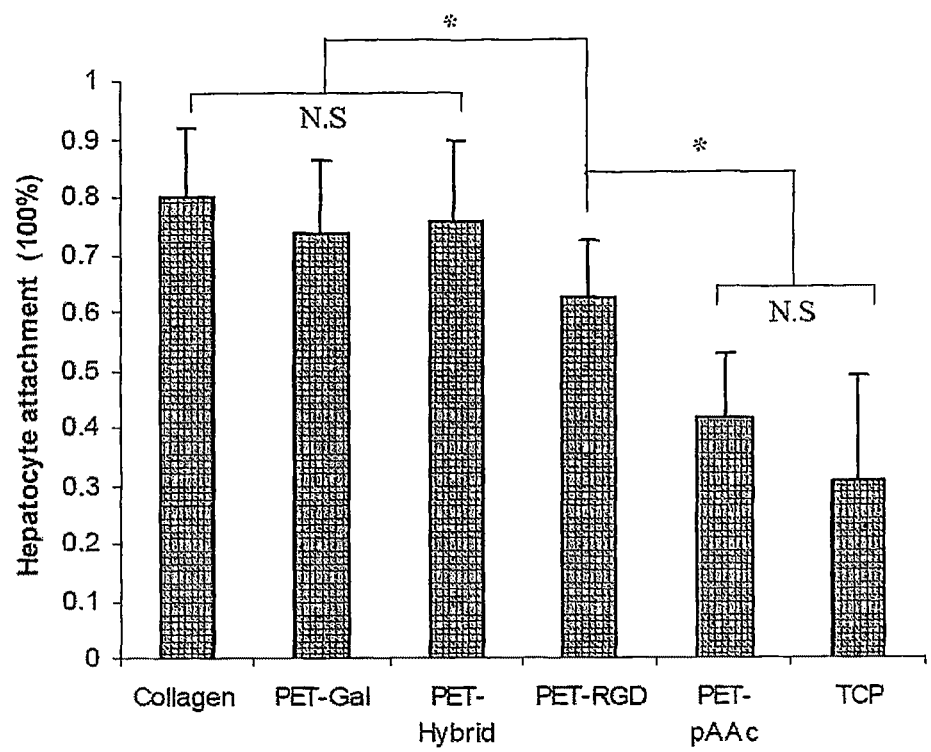
FIG. 10. (A) Attachment of hepatocytes on different substrates after seeding for 2 hours. Data are means±SD, n10 (*): P<0.05, (**): P<0.01, (N.S): not significant (B) Total DNA content of hepatocytes cultured on different substrata at various time points during 7 days culture to show the hepatocytes attached to different substrata.

As shown in FIG. 10A, ligand conjugation significantly enhanced hepatocyte attachment onto the bioactive substrata after 2 h of seeding. Hepatocytes attached to PET-Gal, PET-Hybrid and collagen reasonably to PET-RGD but only poorly to pAAc-PET and Tissue culture plate (TCP). Similar numbers of hepatocytes attach to PET-Hybrid with RGD:Gal ratios of 1:5, 5:1 or 1:1.

Figure 10B:
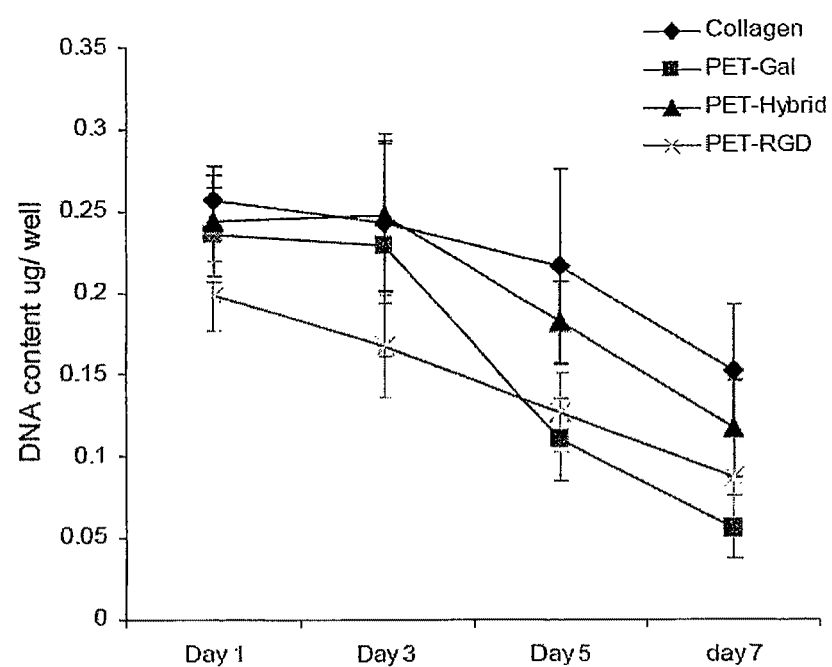

Cultured hepatocytes showed different attachment onto various substrata during 7 day culture as shown by the total DNA content change (FIG. 10B). Total DNA content was used as an estimate of viable cells attached to the substratum [Dunn et al., Faseb J, 1989, February; 3(2):174-177; Hasirci et al, Tissue Eng, 2001, August; 7(4)385-394]. The gradual decrease of total DNA content was considered to be mainly due to cell loss during the daily change of medium. As the 3D spheroids began to detach from the substratum after day 3, a steep drop in DNA content of hepatocytes cultured on PET-gal was seen from day 3 onwards. While on the other substrata, a smooth drop in DNA content was observed. The low total DNA content of hepatocytes cultured on PET-RGD was due to the lower cell number initially seeded. Hepatocytes cultured on collagen substratum and PET-hybrid showed significantly better attachment than on PET-Gal from Day 5 onwards (P<0.01) during one week culture. The results showed enhanced cell attachment after seeding due to presence of the bioactive ligands (RGD peptide, galactose ligand, or RGD/galactose hybrid).

Example 2B

Morphological Changes of Hepatocytes on Bioactive Substrata Over Time

A significant influence of the substratum characteristics, such as the presence of conjugated bioactive ligands on hepatocyte morphologies was observed.

Figure 11:
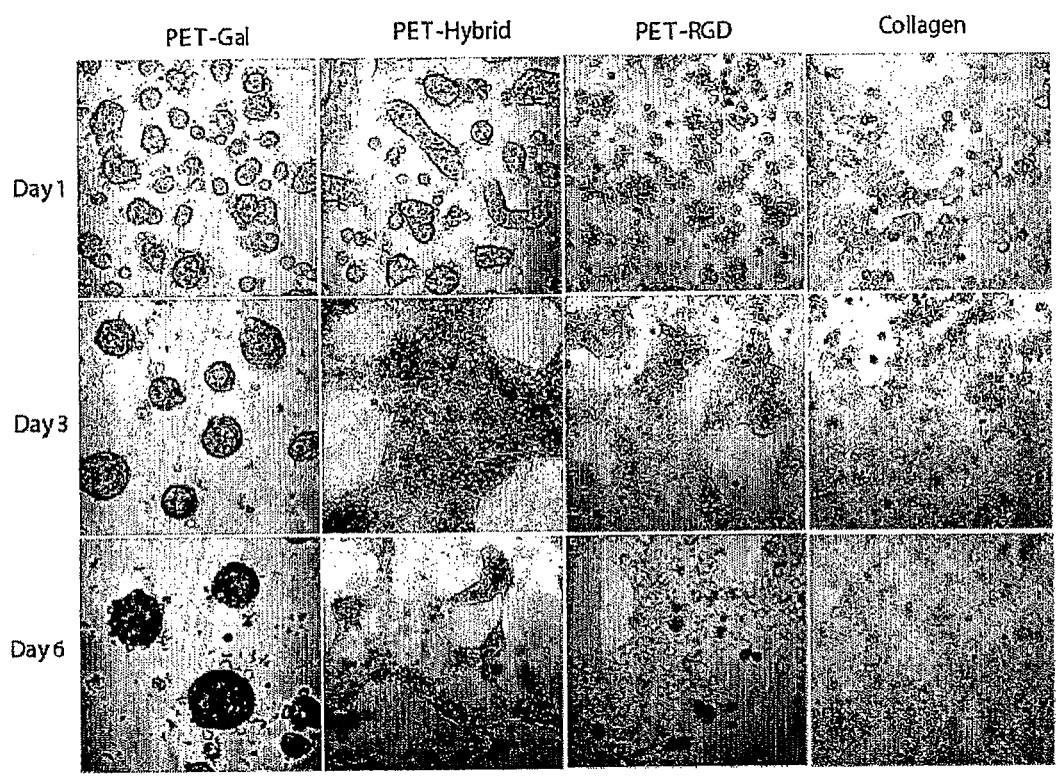
FIG. 11. Phase contrast images of primary hepatocytes cultured on different substrate at various time points during 7 days culture (scale bar=5 μm)

FIG. 11 presents phase contrast images of the cultured hepatocytes at day 1, day 3 and day 6 after cell seeding. Within one day after seeding, hepatocytes formed small pre-spheroids on PET-Gal and non-spreading aggregates on PET-Hybrid (RGD:Gal=1:1) while hepatocytes started to spread on PET-RGD and collagen substratum.

After 3 days' culture, less compact 3-D spheroids were formed on PET-Gal some of which detached from the substratum. Hepatocyte on PET-Hybrid formed less-spreading 2D monolayer with distinct cell-cell boundary. Hepatocytes were fully-spread and flattened on the PET-RGD and collagen substratum to form confluent monolayer.

At day 6, mature spheroids were observed on PET-Gal most of which detached from the substratum. Hepatocyte monolayers cultured on PET-Hybrid stretched to 'island-like' monolayers which were distinct from the fully spreading 2D monolayers of hepatocytes cultured on PET-RGD and collagen. The stretched island-like' monolayers on PET-hybrid could be maintained for at least 1 week before cells detached from the substratum. The dynamic morphology of hepatocytes cultured on PET-Hybrid is termed a '3D monolayer'; this was distinct from the spreading 2D monolayer seen on PET-RGD and a collagen substrata. No significant morphological difference of hepatocytes cultured on PET-Hybrid with different RGD peptide was observed. Therefore, only the hybrid substratum with 1:1 ratio of RGD:Gal was used for hepatocyte cultures in the studies described herein. The results showed that the 3D hepatocyte monolayer can be stabilized on the PET-Hybrid.

Example 2C

Figure 12:
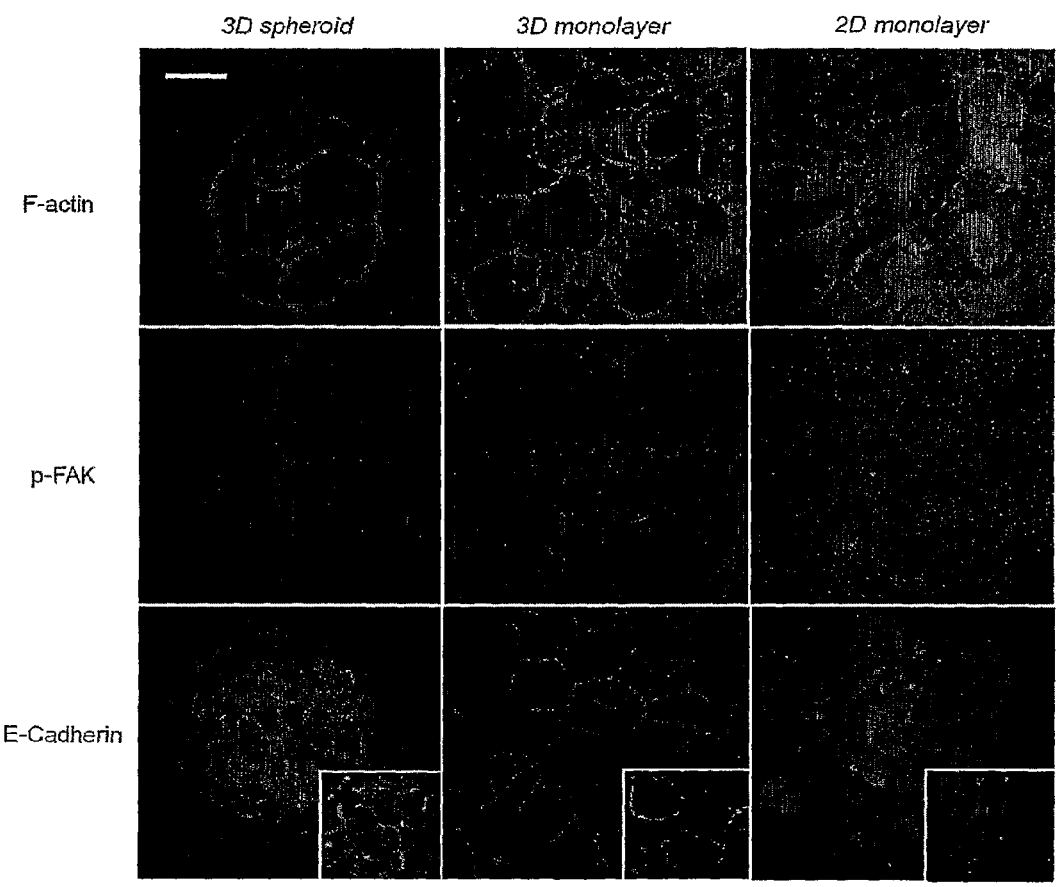
FIG. 12. Confocal-Z-stack projection images of F-actin, p-FAK and E-Cadherin of hepatocytes after 3-day culture as the 3D spheroid, 3D monolayer and 2D monolayer (scale bar: 20 μm); To clearly show the E-Cadherin distribution, part of a single slice from the Z-stack images was put on the corner of the corresponding projection image.

F-actin, p-FAK and E-cadherin Distributions and Expression of Hepatocytes Cultured on Bioactive Substrata Without being bound to any proposed mechanism of action, it is believed that the hepatocytes cultured on PET-Hybrid experience stronger cell-cell interactions and weaker cell-substratum interactions than 2D monolayers which allows the cultured hepatocytes on PET-Hybird to maintain 3D cell morphology. The 3D monolayer cultured on PET-Hybrid should also have a stronger cell-substratum interaction than the 3D spheroids on PET-Gal so as to adhere better to the culture substrata as observed above. The 2D monolayer of hepatocytes cultured on collagen substratum showed intense actin stress fibers throughout the cells indicating strong cell-substratum interaction (FIG. 12). Hepatocytes cultured as the 3D monolayer on PET-Hybrid had less actin stress fibers than the 2D monolayer on collagen substratum but more stress fibers than the 3D spheroids, indicating an intermediate strength of cell-substratum interaction. The 3D monolayer on PET-Hybrid exhibited cortical F-actin distribution similar to the 3D spheroids cultured on PET-Gal indicating strong cell-cell interaction characteristic of hepatocytes in vivo. The p-FAK distribution as intracellular clusters is a specific indicator of the cell-substratum interaction. The punctate p-FAK cluster signals were strong in the 2D and 3D monolayers and very weak in the 3D spheroids (FIG. 12) confirming that the 3D monolayer experienced stronger cell-substratum interaction and could adhere better to the substrata than the 3D spheroids. E-Cadherin expression as a specific indicator of cell-cell interaction was investigated. E-Cadherin was found to localize at the cell-cell boundaries in 3D monolayer and spheroids but intracellularly throughout the hepatocyte cytoplasm in the 2D monolayer. This confirms the stronger cell-cell interaction in the 3D monolayer and spheroids than the 2D monolayer.

Example 2D

Stabilization and De-stabilization of the Pre-spheroid 3D Monolayer

Without being bound to any proposed mechanism of action, the role of the GRGDS (SEQ ID NO:3) peptide in this hybrid substratum is believed to stabilize the 'monolayer' stage through binding with the integrin membrane receptors and to prevent the unfolding of the 'monolayer' into 3D spheroids.

As shown in example 2B, hepatocytes which maintained a monolayer configuration without spheroid formation for up to 1 week before they detached from the substratum. The role of the GRGDS (SEQ ID NO:3) peptide in the PET-Hybrid described herein might be to enhance the cell-substratum interactions through binding the integrin membrane receptors of the hepatocytes and thus may prevent the pre-spheroid hepatocyte monolayer from foiming 3D spheroids.

Figure 13A:
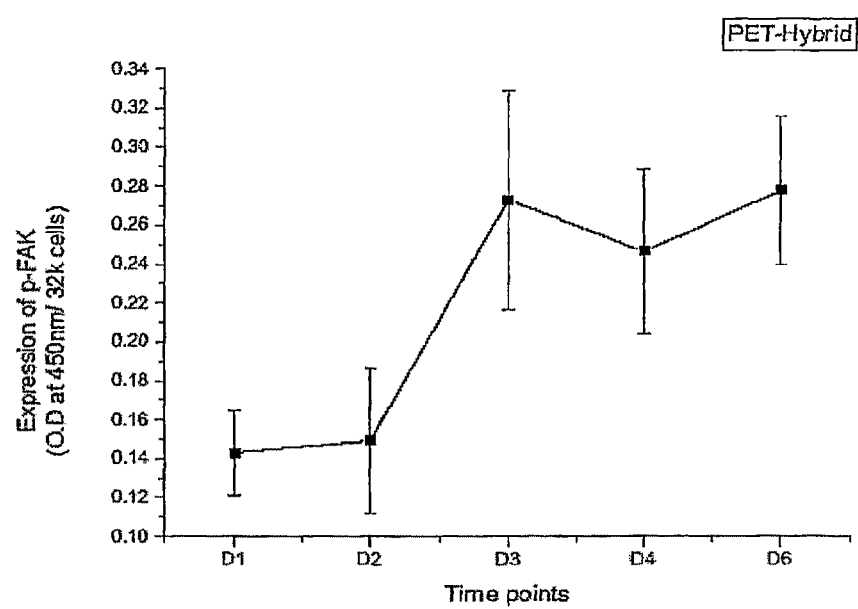
FIG. 13. Stabilization of pre-spheroid 3D monolayer on a hybrid GRGDS/Galactose-PET substratum (PET-Hybrid) which could be destabilized by soluble GRGDS (SEQ ID NO:3) peptide. (A) p-FAK expression of hepatocytes cultured on PET-Hybrid over 6 day culture indicated enhanced cell-substratum interactions of the stabilized 3D monolayer on PET-Hybrid. (B) Phase-contrast images of hepatocytes at day 4 on PET-Gal, PET-Hybrid and collagen substratum in medium with soluble GRGDS (SEQ ID NO:3) peptide and normal medium as control.

This was examined by first quantifying p-FAK expression using ELISA (see Example 1E for description of the method) on the hepatocytes which were cultured for a week on PET-Hybrid. p-FAK expression of the hepatocytes gradually increased during the first 3 day (i.e. D3) culture on PET-Hybrid, and was sustained over 6 days (i.e. D6; FIG. 13A). In contrast to the decrease of p-FAK expression as 3D spheroid formation on PET-Gal at 3 days (FIG. 6A), sustained p-FAK expression of the hepatocytes on the PET-Hybrid suggested enhanced cell-substratum interactions allowing the introduction of GRGDS (SEQ ID NO:3) peptide.

Figure 13B:
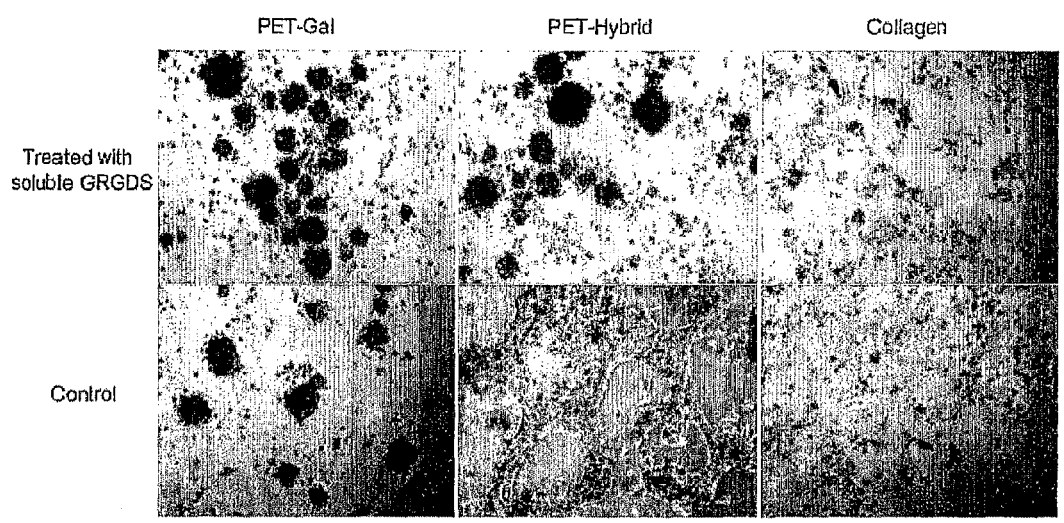

Soluble GRGDS (SEQ ID NO:3) peptide was added to the culture media to potentially compete with the conjugated GRGDS (SEQ ID NO:3) peptide on the PET-Hybrid (FIG. 13B) in order to see if GRGDS (SEQ ID NO:3) was responsible for stabilizing the pre-spheroid monolayer.

Soluble GRGDS (SEQ ID NO:3) peptide, at a 100 μM concentration, destabilized the hepatocyte monolayer maintained on PET-Hybrid allowing the formation of compact 3D spheroids, presumably competing with the conjugated GRGDS (SEQ ID NO:3) peptide for binding sites on the hepatocyte cell surface. Soluble GRGDS (SEQ ID NO:3) peptides also facilitated the detachment of 3D spheroids cultured on PET-Gal from the substratum. Treatment of the soluble GRGDS (SEQ ID NO:3) for 24 h also caused slight toxicity to the hepatocytes as more single dead cells were observed in the treated samples than in the controls. In contrast, soluble galactose ligands did not induce any morphological changes of the 3D spheroids on the galactosylated substratum or the pre-spheroid monolayer on the hybrid substratum or the 2D hepatocyte monolayer on collagen substratum.

Example 2E

Hepatocyte Functions in Response to Bioactive Substrata

The liver-specific functions of stabilized 3D hepatocyte monolayers on PET-Hybrid were investigated.

Total DNA content per sample measured by the PicoGreen DNA assay was used to normalize the function data to account for the cell loss from different substrata throughout the 7-day culture [Dunn et al., Faseb J, 1989, February; 3(2):174-177; Jiang et al., Tissue Eng, 2004, September-October; 10(9-10):1577-1586].

Figure 14A:
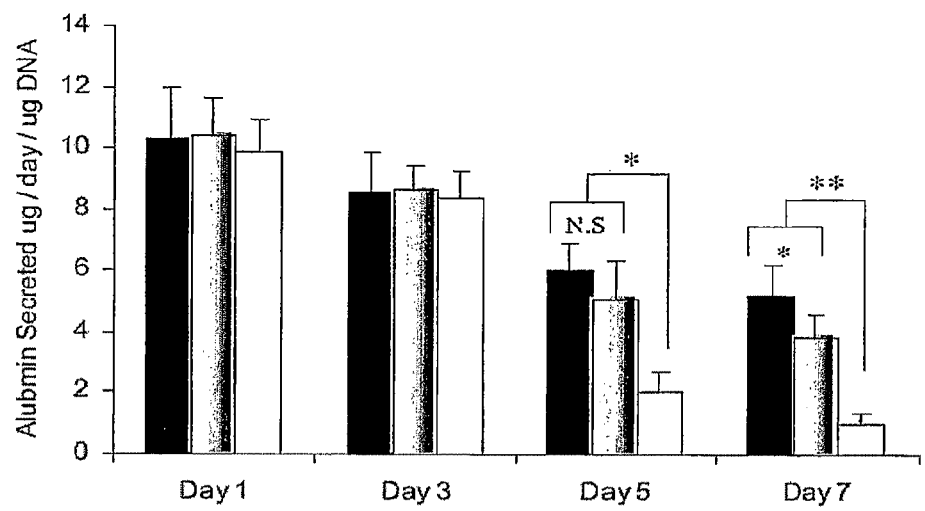
FIG. 14. (A) Albumin secretion level, (B) urea synthesis and (C) 3MC-induced EROD activity of hepatocytes on different substrata at various time points during 7 days culture. The functional data were normalized against the total amount of DNA per sample. Data are means+SD, n=6. (*): p<0.05, (**): p<0.01, (N.S): not significant.
Figure 14B:
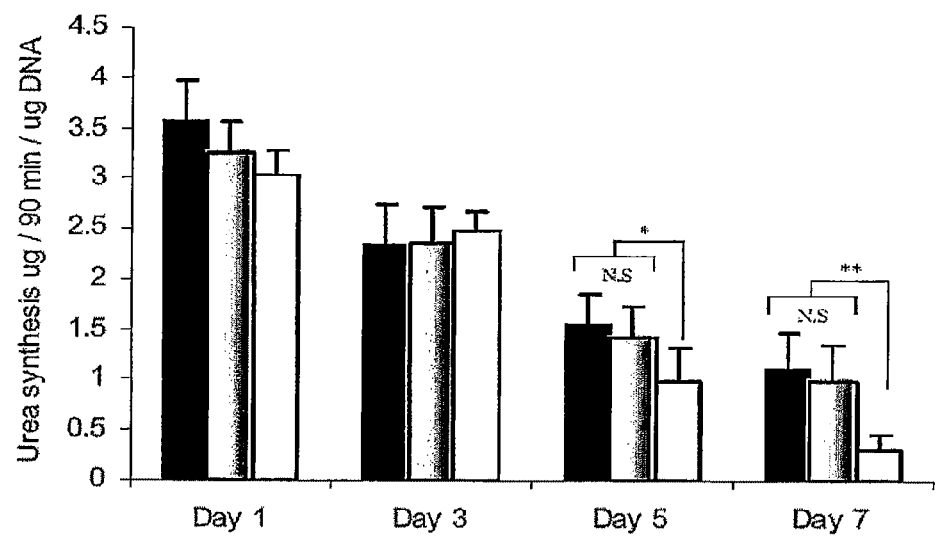
Figure 14C:
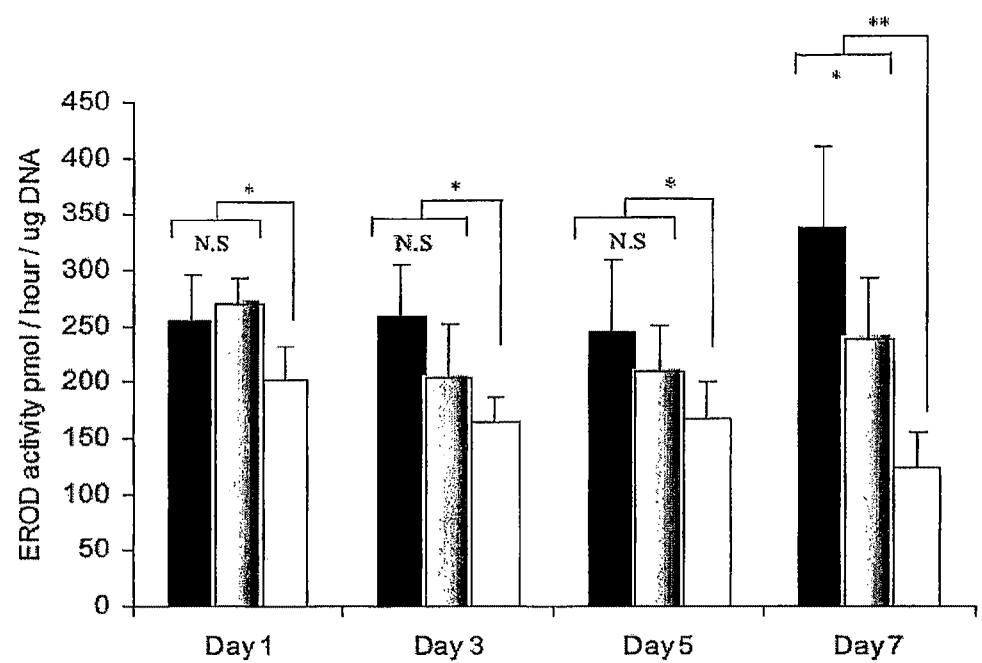

As shown in FIGS. 14A and 14B, the albumin and urea secretion of hepatocytes cultured on PET-Gal and PET-Hybrid was higher than those cultured on collagen substratum over 7 days of culturing. There were significant differences from day 3 to day 7 where albumin and urea secretion of hepatocytes cultured on collagen decreased dramatically. Cytochrome P450s belong to a class of constitutive and inducible haemoprotein enzymes that metabolize many endogenous substrate as well as numerous xenobiotics and therapeutic agents including acetaminophen which is the model drug of the following hepatotoxicity study [Black S D, Faseb J, 1992]. CYPIA is the primary enzyme responsible for the metabolism of 7-ethoxyresorufin-O-deethylation (EROD) and the activity of the enzyme is known to be induced by 3-MC. As shown in FIG. 14C, hepatocytes cultured on all substrata could maintain induced EROD activity over 7 days' culture. The induced EROD level was significantly higher with hepatocytes cultured on PET-Gal and PET-Hybrid than on collagen substratum.

Example 2F

Response to the Acetaminophen-induced Hepatotoxicity by Hepatocytes Cultured on Various Substrata The effect of hepatotoxicity caused by APAP alone and co-administration with 3MC on 3D hepatocyte monolayers cultured on PET-Hybrid as compared with 3D spheroids cultured on PET-Gal and 2D hepatocyte monolayers on collagen substratum was investigated. The co-administration of 3-MC, an inducer of CYP 1A was conducted as the evaluation of drug-drug interaction which would lead to higher toxicity. The hepatotoxicity testing of acetaminophen was carried out according to the methods described in Example 1H.

Figure 15A:
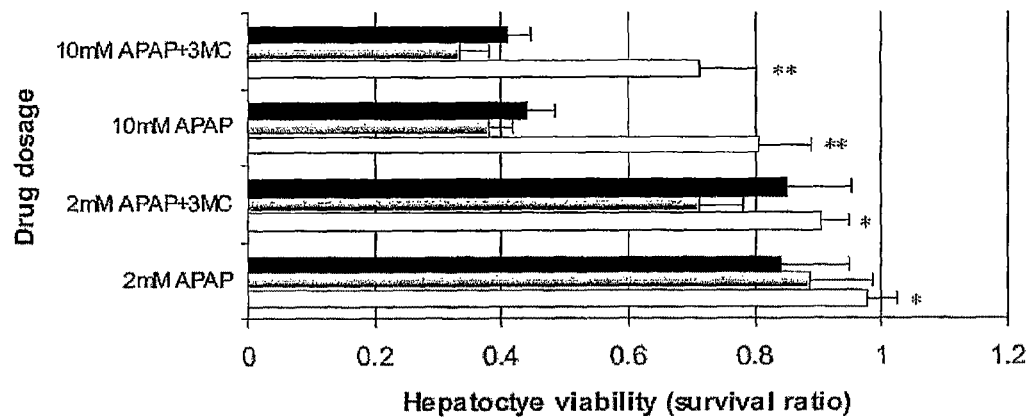
FIG. 15. Response to the acetaminophen-induced hepatotoxicity of hepatocytes cultured on different substrata. MTS assays to show the cytotoxicity of cultured hepatocytes under 24 hours (A) and 48 hours' dosage (B) of different concentration of APAP and APAP co-administered with 3MC. Data are means±SD, n=10 (*): P<0.05, (**): P<0.01, (N.S): not significant.
Figure 15B:
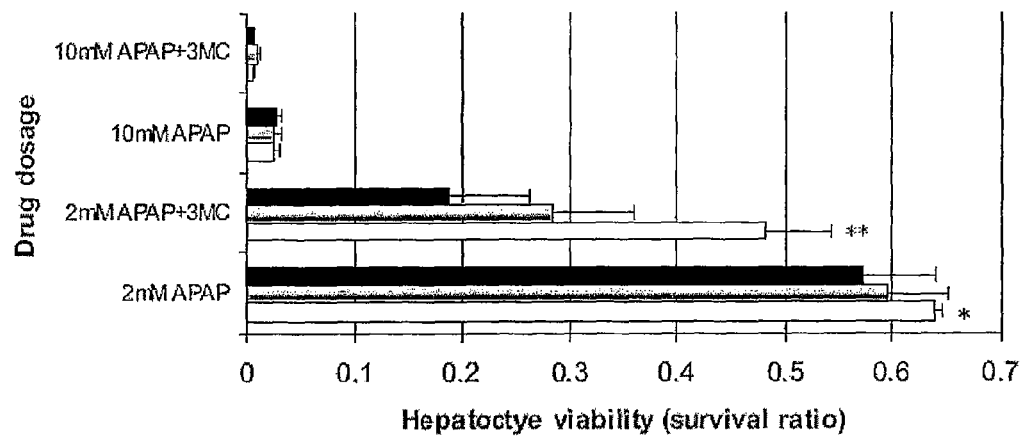

FIG. 15 shows the survival ratio of hepatocytes cultured on different substrata after exposure to APAP or APAP co-administered with 3MC for 24 h (FIG. 15A) or 48 h (FIG. 15B) before conducting the MTS viability assay. In a drug-free condition, hepatocytes cultured on all substrata showed similar readings in MTS viability assay indicating that the basal levels of viability were similar. In all drug dosage conditions described herein, hepatocyte 3D monolayers cultured on PET-Hybrid showed similar responses to hepatotoxicity as developing hepatocyte spheroids which were cultured on PET-Gal. Both of these cultures were more 'hepatotoxicity-sensitive' than 2D monolayers cultured on collagen substrata. Exposure to low concentration of APAP (2 mM) for 24 h was almost non-toxic to hepatocytes cultured on collagen substrata (survival ratio 98%) but slightly toxic to the cells on PET-gal (survival ratio 84%) and PET-Hybrid (survival ratio 89%). A 48 hour exposure to 2 mM APAP caused considerable hepatotoxicity to hepatocytes cultured on collagen (survival ratio 64%) and more severe toxicity to hepatocytes cultured on PET-gal (survival ratio 57%) and PET-hybrid (survival ratio 59%). When exposed to high concentrations of APAP (10 mM) for 24 h, hepatocytes cultured on PET-Gal (survival ratio 44%) and PET-Hybrid (survival ratio 38%) demonstrated about twice the sensitivity to hepatotoxicity than hepatocytes cultured on collagen substratum (survival ratio 80%). 48 h exposure to 10 mM APAP killed most of the cells on different substrata.

The amplified effect of hepatotoxicity of 3MC when coadministered with APAP was not shown clearly at 24 h but was significant after 48 h. Almost all cells died when exposed to 10 mM APAP plus 3MC on different substrata. When exposed to 2 mM APAP plus 3MC for 48 h, hepatocytes cultured on PET-Gal (survival ratio 19%) and PET-Hybrid (survival ratio 28%) were almost three times and two times more sensitive respectively to hepatotoxicity than hepatocytes cultured on collagen substratum (survival ratio 48%).

The invention claimed is:

1. A synthetic surface comprising (i) a polyethylene terephthalate substrate with polyacrylic acid grafted thereto (pAA-g-PET) and (ii) sugar groups and peptide groups, wherein the sugar groups and the peptide groups are separately conjugated to said substrate via amide bonds, wherein the sugar groups consist of 1-O-(6'-aminohexyl)-D-galactopyranoside (AHG) and are present at a density selected from group consisting of:
  (i) about 6.2 nmol/cm$^2$ to about 7.68 nmol/cm$^2$;
  (ii) about 3.91 nmol/cm$^2$ to about 4.81 nmol/cm$^2$;
  (iii) about 4.49 nmol/cm$^2$ to about 6.27 nmol/cm$^2$; and
  (iv) about 5.18 nmol/cm$^2$ to about 6.66 nmol/cm$^2$;

and wherein the peptide groups consist of an Arginine-Glycine-Aspartic acid (RGD) peptide group having an amino acid sequence GRGDS (SEQ ID NO: 3) and optionally further comprising a YIGSR peptide (SEQ ID NO: 1) and/or GFOGER peptide (SEQ ID NO: 2), and wherein the peptide groups are present at a density selected from the group consisting of:
(i) about 4.77 nmol/cm$^2$ to about 6.49 nmol/cm$^2$;
(ii) about 16.21 nmol/cm$^2$ to about 22.59 nmol/cm$^2$;
(iii) about 0.82 nmol/cm$^2$ to about 1.8 nmol/cm$^2$; and
(iv) about 6.08 nmol/cm$^2$ to about 8.0 nmol/cm$^2$;
and wherein said sugar groups and said peptide groups are present at a ratio selected from the group consisting of about 5:1, about 1:1, and about 1:5, to form a pre-spheroid three dimensional (3D) monolayer which is prolonged for a period of at least 24 hours when hepatocytes are cultured on the surface.

2. The synthetic surface according to claim 1 wherein the surface is porous.

3. A synthetic surface according to claim 1 wherein:
(i) the sugar groups are present at a density of about 6.2 nmol/cm$^2$ to about 7.68 nmol/cm$^2$ and the peptide groups are present at a density of about 4.77 nmol/cm$^2$ to about 6.49 nmol/cm$^2$;
(ii) the sugar groups are present at a density of about 3.91 nmol/cm$^2$ to about 4.81 nmol/cm$^2$ and the peptide groups are present at a density of about 16.21 nmol/cm$^2$ to about 22.59 nmol/cm$^2$;
(iii) the sugar groups are present at a density of about 4.49 nmol/cm$^2$ to about 6.27 nmol/cm$^2$ and the peptide groups are present at a density of about 0.82 nmol/cm$^2$ to about 1.8 nmol/cm$^2$; or
(iv) the sugar groups are present at a density of about 5.18 nmol/cm$^2$ to about 6.66 nmol/cm$^2$ and the peptide groups are present at a density of about 6.08 nmol/cm$^2$ to about 8.0 nmol/cm$^2$.

4. A synthetic surface according to claim 1 wherein the sugar groups are present at a density of about 6.2 nmol/cm$^2$ to about 7.68 nmol/cm$^2$ and the peptide groups are present at a density of about 4.77 nmol/cm$^2$ to about 6.49 nmol/cm$^2$, and wherein the sugar groups and the peptide groups are present at a ratio of about 1:1.

5. A synthetic surface according to claim 1 wherein the sugar groups are present at a density of about 3.91 nmol/cm$^2$ to about 4.81 nmol/cm$^2$ and the peptide groups are present at a density of about 16.21 nmol/cm$^2$ to about 22.59 nmol/cm$^2$, and wherein the sugar groups and the peptide groups are present at a ratio of about 1:5.

6. A synthetic surface according to claim 1 wherein the sugar groups are present at a density of about 4.49 nmol/cm$^2$ to about 6.27 nmol/cm$^2$ and the peptide groups are present at a density of about 0.82 nmol/cm$^2$ to about 1.8 nmol/cm$^2$, and wherein the sugar groups and the peptide groups are present at a ratio of about 5:1.

* * * * *